US006787366B1

(12) United States Patent
Novak

(10) Patent No.: US 6,787,366 B1
(45) Date of Patent: Sep. 7, 2004

(54) MICROSPOT TEST KIT AND METHOD FOR CHEMICAL TESTING

(75) Inventor: Thaddeus John Novak, Bel Air, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/340,165

(22) Filed: Jun. 28, 1999

Related U.S. Application Data

(63) Continuation-in-part of application No. 08/763,181, filed on Dec. 11, 1996, now Pat. No. 5,935,862.

(51) Int. Cl.[7] .............................................. G01N 33/00
(52) U.S. Cl. ....................... 436/162; 436/104; 436/166; 436/169; 210/658; 210/634; 422/68.1; 422/70; 422/61; 422/58
(58) Field of Search ................................ 210/656, 658, 210/634, 635; 422/56–58, 61, 68.1, 70; 436/104, 162, 164, 166, 169

(56) References Cited

U.S. PATENT DOCUMENTS

| 4,346,001 A | * | 8/1982 | Tyihak et al. ................ 210/658 |
| 4,428,908 A | * | 1/1984 | Sahley et al. ................. 422/61 |
| 5,935,862 A | * | 8/1999 | Novak .......................... 436/104 |
| 6,420,181 B1 | * | 7/2002 | Novak .......................... 436/104 |

* cited by examiner

Primary Examiner—Lyle A. Alexander
(74) Attorney, Agent, or Firm—William Randolph; John Biffoni

(57) ABSTRACT

A method, system and kit for detecting the presence of an analyte includes placing a solution containing the analyte in a microcapillary tube and placing the microcapillary tube in contact with a layer of sorbent material so that the solution is withdrawn from the microcapillary tube by capillary action. A detector reagent which has been pre-deposited on the sorbent material indicates the presence of the analyte. The sorbent material, detector reagent, and the solvent for the analyte solution are selected so that the solvent is absorbed into the sorbent material and the analyte is adsorbed by the sorbent material and concentrated at the spot where the detector reagent has been pre-deposited and where the microcapillary tube contacts the sorbent material.

26 Claims, 6 Drawing Sheets

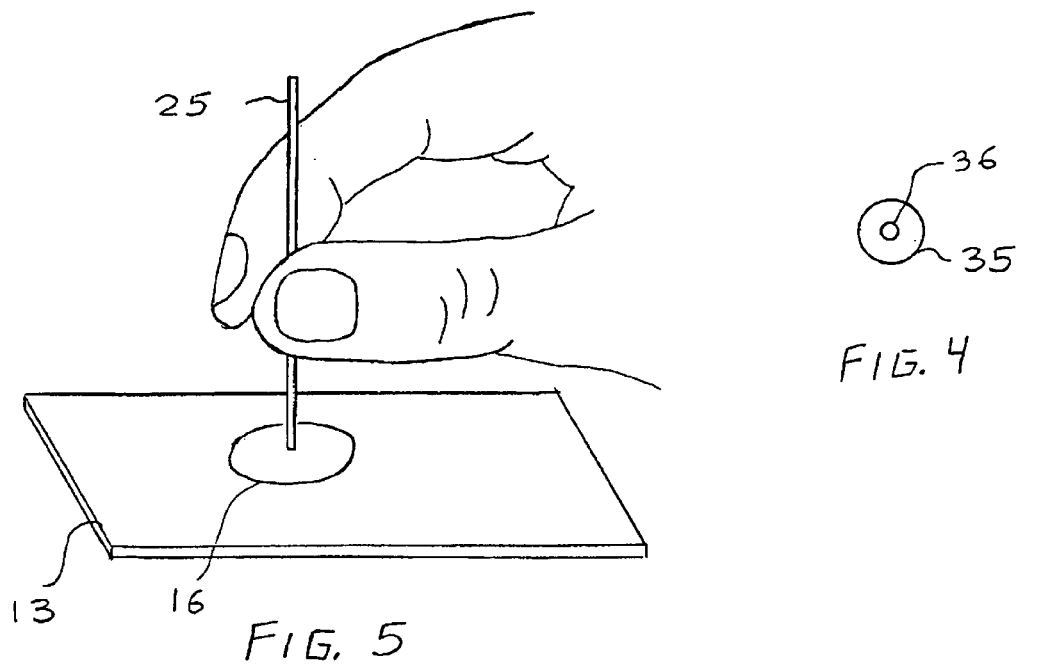
FIG. 4
FIG. 5
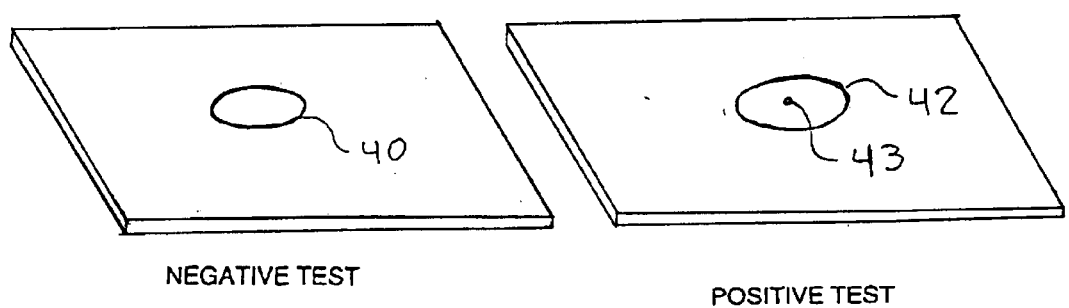
NEGATIVE TEST
POSITIVE TEST
FIG. 6

STEP 1

STEP 2

MICROSPOT TEST KIT AND METHOD FOR CHEMICAL TESTING

This is a Continuation-In-Part of U.S. application Ser. No. 08/763,181, filed Dec. 11, 1996 and now U.S. Pat. No. 5,935,862. A application is U.S. application Ser. No. 09/296,602, filed Apr. 23, 1999 and now U.S. Pat. No. 6,420,181.

GOVERNMENT INTEREST

The invention described herein may be manufactured, licensed, and used by or for the U.S. Government.

BACKGROUND OF THE INVENTION

1. Field of the Invention

This invention relates to a field test kit and method of on-site testing for the presence of contaminants and chemicals and, more particularly, to a micro spot method for detecting the presence of a variety of chemicals and environmental contaminants.

2. Description of the Prior Art

In view of biological hazards associated with toxic chemicals and environmental contaminants, regulations have been established by legislatures and environmental agencies to monitor a wide variety of chemicals and their byproducts. As a result, it is often necessary to conduct on-site inspections and analyses of various chemical spills, dump sites, and manufacturing facilities to detect environmental contaminants, hazardous conditions and to assure compliance with environmental regulations Advantages of on-site inspection and analysis of chemical sites include resolving ambiguities during the inspection, reducing the potential for contamination and cross-contamination of samples during travel to off-site testing laboratories, and providing a convenient method of performing a large number of preliminary tests to detect and screen for chemical contaminants. On-site inspection also provides a rapid indication of those samples which may possibly contain compounds that must be identified using more sophisticated laboratory analytical techniques. On-site testing also allows the level of concentration and spread of contamination from chemical spills to be readily surmised.

Reagent-based chemical detection and chromatographic methodologies are attractive for on-site testing and screening because many tests can be run in a short period of time and they are capable of providing visual presumptive evidence of the presence of a chemical substance in a sample. One methodology comprises classical spot tests that are normally carried out in depressions or wells of a porcelain spot plate. Conventionally, small amounts of a solution, which may contain chemical contaminants, are placed in the wells of the spot plate. Small quantities of different reagents are then added to the solution samples and a positive test is normally signified by a color change in the well of the spot plate. An advantage with these tests is that a number of tests can be carried out on a single plate. For example, as many as 12 different spot tests can be carried out on a small 3.5×4.5 inch spot plate. Another advantage is that it is possible to rapidly screen a large number of samples during a short period of time. However, as the concentration of the chemical substances become more dilute, it becomes more difficult to reliably detect the presence of the chemical substances. In most cases, the lower limit of detection is in the 1–100 microgram range.

Another methodology for screening samples and detecting target analytes in samples involves the use of thin layer chromatography (or TLC), which conventionally utilizes a plate having a surface layer formed of a sorbent material or gel. In order to separate the components of the analyte obtained from a sample, a drop of solution is carefully applied above the bottom edge of a thin layer chromatography plate. Solutions suspected of containing target analytes are preferably deposited onto the surface of a TLC plate in the form of a drop to avoid a streaking pattern that would result if the device for applying the drop actually contacts the surface of the plate while a sample solution is being deposited. After the solvent evaporates, the residue on the plate is eluted with another solvent or solvent mixture (also known as the eluant) thereby causing the chemical components of the sample to migrate towards the top or opposite edge of the plate. When the proper conditions and eluant are chosen, each analyte migrates across the plate at a rate that is different from the other analytes. The elution step results in the different analytes separating from each other and settling at different regions as diffuse spots along the path of migration. After the elution step, the plates are allowed to dry and then they are sprayed with a solution of a visualization reagent (detector reagent). A persistent concern with thin layer chromatography is that the elution step of waiting for the solvent to completely wet the plate and for the analytes to migrate and separate is relatively time-consuming. In many instances, proper completion of the elution phase may exceed an hour and warrant involved techniques and quality control steps to assure adequate separation of the different analytes. Another concern involves situations where the analytes are present in such low concentrations that the detection signals obtained in the tests are weak and can possibly be misread. In summary, with thin layer chromatography the analytes in the sample migrate and separate into localized regions, as opposed to remaining concentrated at spots or points.

In testing a sample solution for the presence of an analyte, much effort is often expended in preparing the reagent solutions used to detect the analyte. In order to maximize shelf-life storage stability, the detector reagents required for the tests are stored in the dry state and preferably in an inert atmosphere. When a reagent solution is required, a predetermined amount of dry reagent is mixed with an appropriate solvent to form a reagent solution having a particular concentration. In conducting tests at field sites that are remote from a laboratory, the time required to prepare several reagent solutions, take precautions to avoid spillage and dispose of excess reagent solutions after completing the tests may exceed the time actually devoted to testing a sample solution for an analyte.

For various tests, reagents have been pre-deposited in suitable mediums. Litmus paper is an example. Other examples are disclosed in U.S. Pat. No. 4,301,027 assigned to Dynamit Nobel AG and a divisional patent, U.S. Pat. No. 4,436,823 assigned to Dragerwerk Aktiengesellschaft where silica gel materials incorporate insolubilized reagents for colorimetric testing. A further example is set forth in U.S. Pat. No. 5,308,495 where doped sol-gel glasses contain colorimetric reagents. A more recent example is set forth in U.S. Pat. No. 5,824,526, which discloses that sol-gel glass forms a solid support for reagents which are trapped therein. Examples of literature related to the use of dry reagents and chemical testing include: Dry Reagent Chemical Tests, Analytical Communications, 34, 1H-3H (1997) by T. E. Edmonds, J. M. Lee, and J. D. Lee; Solid Phase Chemistry: Its Principles And Applications In Clinical Analysis, Talanta 31, 863(1984) by A. Zipp and W. E. Hornby; Chemistry On A Stick (Part 1), Chemtech 21, 462 (1991) by E. Diebold, M.

Rapkin and A. Usmami; and Chemistry On A Stick (Part 2), Chemtech 21, 547 (1991) by A. Burke, J. DuBois, A. Azhar and A. Usmani. To improve shelf-life stability of detector reagents predeposited on a test medium, such as a plate containing a chromatographic silica gel medium with different reagents pre-deposited in the silica gel, the test medium can be sealed, preferably in an inert atmosphere, to prevent oxidation, hydrolysis or other types of degradation of the dry detector reagents. This may include sealing the silica gel plates in a plastic bag under a vacuum and in an inert atmosphere, as discussed for example in U.S. Pat. No. 5,837,288.

Other disclosures generally related to dry reagent tests include U.S. Pat. Nos. 4,729,959, 4,755,472, 4,843,377, 5,190,863, 5,326,697, 5,330,715, 5,418,141, 5,498,547, 5,510,245, 5,610,072, 5,656,739, 5,739,305, 5,756,296, 5,801,061, 5,824,491, 5,846,754, 5,856,199, and 5,848,797.

SUMMARY OF THE INVENTION

The micro spot test system and methodology of the present invention relates to an apparatus and method for the testing of analytes contained in a sample by dissolving the analytes in a solvent and utilizing capillary deposition techniques to concentrate the analytes on sorbent materials. Detector reagents are pre-deposited on the sorbent materials to form different reaction sites or regions for receiving the solution containing the analytes. Detection sensitivity and accuracy for a range of concentrations of analytes is provided by applying by capillary deposition a solution containing the analytes to different regions of the sorbent layer that contain detector reagents so that the analytes in the solution become concentrated at the particular spot or point of deposition on the sorbent layer. The solutions are deposited by placing small diameter tubes containing the analyte solution in contact with the surface of the sorbent material so that the solutions are drawn from the small diameter tubes by capillary action. The detector reagents in the different reaction sites of the sorbent layer are pre-deposited on the sorbent to detect the presence of the analytes that are concentrated at the spot of the reaction sites where the small diameter tube contacts the sorbent layer.

A system for chromogenically detecting the presence of chemical analytes includes a means for obtaining a sample solution containing the analytes; a device for the capillary deposition of the sample solution; chromatographic sorbent materials; and chromogenic detector reagents which have been pre-deposited on the sorbent materials. Storage devices may be provided for the samples and for the sample solutions, capillary deposition devices, and the chromatographic sorbent materials containing the chromogenic detector reagents.

Accordingly, one object of the present invention is to provide a compact chemical screening apparatus which is of a self-contained, efficient design for rapid screening of solutions for the presence or absence of target analytes.

Another object of the present invention is to provide a chemical screening device which is relatively simple to use for sample solutions containing a wide range of analytes in a wide range of concentration levels.

These, together with still other objects of the invention, along with the various features which characterize the invention, are pointed out with particularity in the appended claims.

BRIEF DESCRIPTION OF THE DRAWINGS

Other objects and advantages of the invention will become apparent upon reading the following detailed description with reference to the attached drawings, wherein:

FIG. 4 is a view of the end portion of a capillary tube;

FIG. 5 is a view generally showing the end portion of a capillary tube in contact with a sorbent layer;

FIG. 6 is a plan view of a sorbent layer depicting the results of a micro spot test;

DETAILED DESCRIPTION OF THE INVENTION

Figure 1:
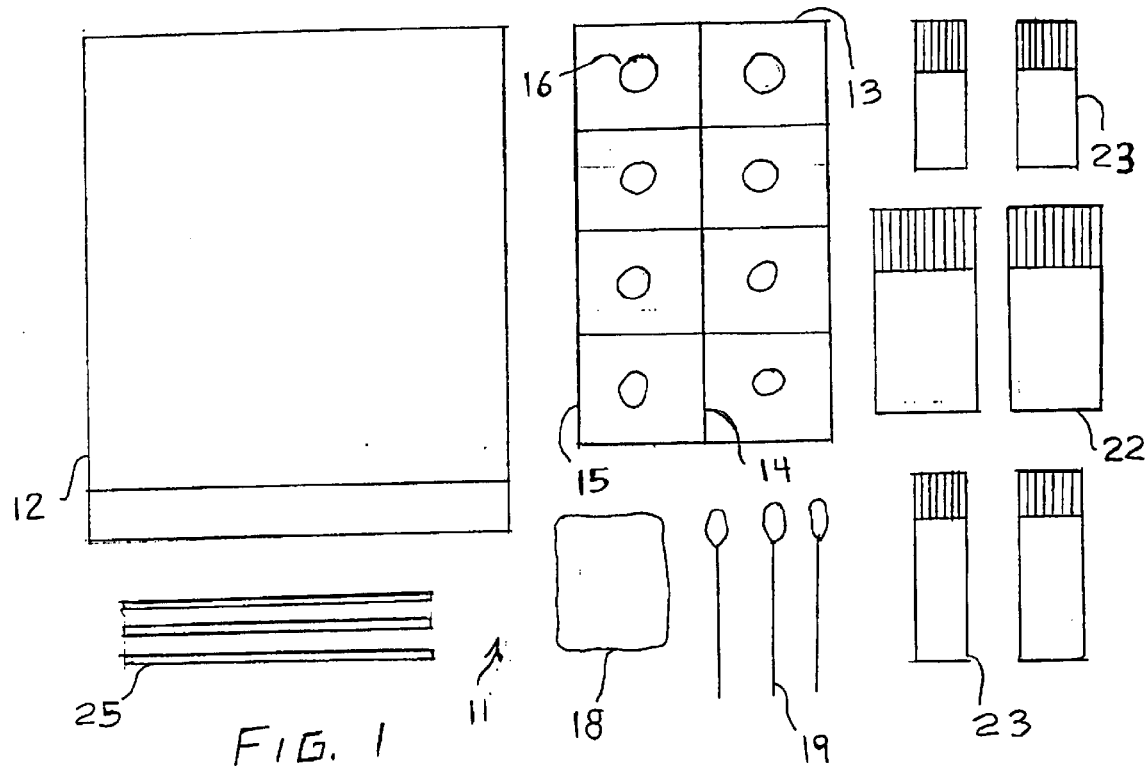
FIG. 1 is a plan view of a field test kit for performing on-site chemical analysis.

The micro spot system and methodology of detecting the presence of target analytes in a sample comprises the application of a solution containing the analytes to a chromatographic sorbent material by capillary action. Sufficient amounts of chromogenic detector reagents to form chromogenic indicators when a target analyte is present in the sample have been pre-deposited on the chromatographic sorbent material at different sites to receive the solution containing the analytes. Apparatus for accomplishing this is generally shown in FIG. 1. In FIG. 1, the apparatus or kit 11 includes a bag or container 12 for storing the components of the system; at least one thin layer chromatographic plate (TLC) plate 13; collecting devices such as cloth wipes 18 or swabs 19 for wiping surfaces for chemical residues; solvent containers 22; containers 23 for receiving the swabs and solvent solutions; and small diameter capillary or microcapillary tubes 25. Solvents for the samples are stored in separate bottles 22. The plate 13 is provided with score lines 14 to divide the plate 13 into a plurality of individual test sites 15. A different reagent has been pre-deposited on each test site 15, as generally depicted by regions 16 in FIG. 1. To ensure long shelf-life stability of the reagents that have been deposited on the sorbent material, the plate 13 could be packaged in a plastic bag which contains and inert gas or which has been vacuum-sealed in an inert atmosphere. Additionally, the plates 13 and test sites 15 can be marked or coded to identify a particular type of test, such as water quality, where the different reagent sites 16 are also identified.

For purposes of this application, the term sample is defined as a representative fraction of the material that is to be processed and tested to detect the presence of an analyte. The sample may be a solid, such as soil, a liquid, such as water taken from a lake, or a vapor, such as fumes obtained from a chemical plant. An analyte is a chemical substance present in the samples that are being tested or analyzed. A solution is a homogeneous liquid that contains dissolved chemical substances. A sample solution is a homogeneous liquid that contains dissolved chemical substances (i.e., the analytes or solutes) and which is derived by washing, extracting, or eluting a sample with a solvent or mixture of solvents. For example, surface wipes 18 or swabs 19 of polyester or similar material are used to obtain a sample by wiping a suspected surface. A sample solution is obtained for analysis by washing, extracting or eluting the wipe in a container 23 with a suitable solvent such as acetone, dichloromethane, hexane, etc. Soil samples can be washed, extracted or eluted in separate containers to obtain sample solutions. Aqueous samples suspected of containing a target analyte can be extracted with an immiscible solvent which is capable of extracting the analytes believed to be therein. In addition, solid phase extraction (SPE) or solid phase microextraction (SPME) techniques can be used to extract analytes from water for analysis using the micro spot tests.

Once the solution or liquid extract has been formed, and where necessary the extract has been concentrated by evaporation, a tube with a small diameter bore or opening 25, such as a small diameter capillary or microcapillary tube is used to collect and dispense small amounts of the sample solution onto the surface of plate 13 by capillary action. Preferably, the plates 13 are thin layer chromatographic plates (or TLC) plates having a surface layer formed of a chromatographic sorbent material. A sorbent material is a material that has both absorption and adsorption characteristics. Absorption is defined as the penetration of liquids into the bulk of a porous material somewhat like a sponge soaking up water. Adsorption is a process whereby a chemical substance, an analyte, sticks, clings or adheres to the surface of a solid constituent, the adsorbent. As noted above and as shown in FIG. 1, the plate 13 is provided with score lines 14 to divide the plate 13 into a plurality of individual test sites 15 where a reagent(s) has been pre-deposited on the different test sites as represented by regions 16. Generally, the amount of sample delivered to a test site on the chromatographic material from a microcapillary tube having a length of one and one quarter inches is on the order of from about 0.1 microliters (for an approximate 0.05 mm diameter microcapillary opening) to about 30 microliters (for an approximate 1.6 mm diameter microcapillary opening) of sample. In most instances sample size will be on the order of from about 0.5 microliters (for an approximate 0.1 mm diameter microcapillary opening) to about 5 microliters (for an approximate 0.4 mm diameter microcapillary opening) and preferably, the sample will be on the order of from about 1 microliter (for an estimated 0.2 mm diameter microcapillary opening) to about 3 microliters (for an estimated 0.25 mm diameter microcap opening). Microcapillary tubes having longer lengths can be used. If desired, the microcapillary tube 25 can be held with commercially available holders or forceps.

Figures 2, 3:
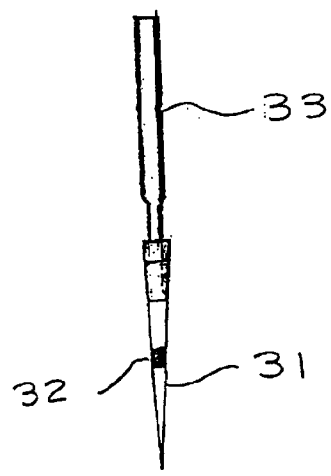
FIG. 2 is a plan view of a pipet with a micro-tip.
FIG. 3 is a plan view of removable micropipet tips.

The term "microcapillary tube" includes any tube made from glass, plastic or other material having a small diameter opening that is capable of dispensing liquid from (or drawing liquid into) the opening by capillary action. Examples of small diameter capillary tubes are those marketed by Drummond and sold under the tradename Microcaps. Another type of tube having a small diameter opening is a micropipet. A micropipet is a glass or plastic tube having a small diameter opening (or capillary opening) at one end and an enlarged opening at the other end of the micropipet, as generally shown by micropipet 27 in FIG. 2. Examples of micropipets are Micro-tip polyethylene pipets sold by Micro Mole Scientific. One benefit of a micropipet is that if the top of the bulb is cut off, as shown in FIG. 2, the larger end functions as a funnel for holding a larger volume of fluid sample than could normally be held or drawn into a capillary tube. Consequently, a larger volume of sample (such as 10 microliters or more) can be used to achieve a higher detection sensitivity with respect to the concentration of analyte that can be detected. Replaceable micropipet tips 31, as shown in FIG. 3, are examples of additional devices that have small diameter openings. A removable micropipet tip 31 would be placed on the end portion of another tube 33 or container so that the liquid in the tube or container would be withdrawn by capillary action when placed in contact with a chromatographic sorbent material. An additional deposition control could be achieved by use of an in-line filter element 32 in a microcapillary device. One example of a micropipet tip is available under the tradename Plastibrand autoclavable nonsealing filter tips and another example of a micropipet tip without a filter is Catalog No. 71-6311-10 from PGC Scientific, Gaithersburg, Md. An example of a micropipet tip with a filter is Catalog No. 71-6311-16 from PGC Scientific, Gaithersburg, Md. While microcapillary tubes, micropipets and micropipet tips have been distributed for use with bulbs or other devices for forcing liquid out of the tubes, use of such pressure devices for forcing liquid from microcapillary tubes is contrary to the methodology of the present invention where the solution containing the analyte is deposited by capillary action. Further, while some methodology for applying a sample to a TLC plate with a microcapillary tube includes moving the tip of the microcapillary tube as the sample is being applied, use of such methodology that includes moving the tip of the microcapillary tube is contrary to the methodology of the present invention where the analyte contained in the sample solution is adsorbed in a small volume of sorbent.

To avoid breaking extremely thin microcapillary tubes, micropipets and micropipet tips during use as the ends portions of these devices contact sorbent surfaces, it is possible to use various holding devices such as forceps and small clamps. While microcapillary tubes have been found acceptable for most applications, where conditions or technique warrant, the end portions of the tubes can be formed with thickened wall portions as shown in FIG. 4, where the thickness of the wall portions 35 are at least equal to the diameter of the opening 36 of the tube 25. Increasing the wall thickness to at least twice the diameter of the opening not only strengthens the end portion of the tubes for adverse use conditions, but also provides a larger contact surface area relative to the size of the opening and thereby promotes higher circumferential contact and seal of the microcapillary tubes with the sorbent material.

In general, the concentration of analyte in solution that is capable of being detected using a microcapillary tube to apply the solution containing the analyte to a thin layer chromatography plate (or TLC plate) in a micro-spot test is inversely related to the total volume of solution applied to the plate. For example, analytes present in solutions at low concentration levels can be detected by increasing the total volume of solution applied by capillary action to a TLC plate in the micro spot test. When using a microcapillary tube such as a micropipet to apply a relatively large volume of solution to a TLC plate, the sample solution being drawn from the tip of the micropipet should initially come in contact only with the area directly beneath the opening of the micropipet that contacts the TLC plate. One way for this condition to be met is that the solution can be added to the large end of the micropipet tube in small aliquots, so that the solution wets the TLC plate by capillary action. Another way for this condition to be met is that when a large volume of solution is added in a single aliquot to the micropipet, sufficient pressure should be exerted so that the micropipet tip completely contacts the TLC plate. When this occurs, the solution will wet the plate by capillary action. To promote well-defined small spots, the liquid solution should not be allowed to leak or flow from the juncture of the micropipet tip with the surface of the chromatographic sorbent layer of the TLC plate. A further methodology is to use a micropipet tip that contains a filter or other device within the tip that slows the flow of solution to ensure that the solution wets the TLC plate by capillary action when the solution is applied to the TLC plate by placing the tip in contact with the sorbent layer of the TLC plate.

Preferably, the sorbent layer should be capable of acting both as an adsorbent and as an absorbent. It is believed that when the sample solution, which contains an analyte (i.e., the solute) dissolved in a solvent, is applied to the sorbent material by capillary action using a microcapillary device, the solute separates from the solution because it adheres or clings to the walls of the pores in a small volume of the sorbent immediately surrounding the point of application of the sample solution due to adsorption and it reacts with the detector reagent to form a chromogenic indicator, while the solvent, a fluid which consequently has been freed from the solute, fills the voids in the pores of the sorbent due to absorption. This phenomenon results in the analyte concentrating within the sorbent layer and being localized in a small volume or "spot" of the sorbent material, while the solvent freely wets a substantial volume of the sorbent material. Since the volume of sorbent material in which the solute or analyte is adsorbed is a small fraction of the volume of sorbent in which the solvent is absorbed, the analyte becomes highly concentrated, and consequently, high sensitivity of detection is made possible with the micro spot tests. When the analyte is present in very low concentration levels, application of the sample solution to the sorbent layer will result in the analyte concentrating in a very small volume of the sorbent material, and hence, will produce only a very small spot. Whereas, if the analyte is present in a somewhat higher concentration level, application of the sample solution to the sorbent layer will result in the analyte concentrating in a somewhat larger volume of the sorbent layer, and hence, will produce a somewhat larger spot. However, visual detection of even the smallest spot has been possible by photographing the microspot test result, and then enlarging the photograph. FIG. 5 depicts a view where the end portion of a microcapillary tube has been placed in sufficient contact with a sorbent layer so that as the solution containing the analyte leaves the opening in the end portion of the tube, the analyte is adsorbed in a small localized region or spot about the point where the tip or end of the microcapillary tube contacts the sorbent layer, while the solvent spreads throughout the porous medium as it wets and is absorbed into the sorbent layer. The ring 16 represents the detector reagent that has been pre-deposited onto the sorbent layer. An actual ring or other markings may be placed on the surface of the sorbent layer to indicate where the reagent has been deposited and where the microcapillary tube should contact the sorbent layer.

The chromatographic sorbent material is preferably a thin-layer chromatography (or TLC) plate. TLC plates are commonly found containing a silica gel or alumina coating. One example is MK6F Silica Gel 60A TLC plates, Catalog No. 4861-110 from Whatman, Inc., Clifton N.J. 07014, which contains a 250 micron thick layer on a 1 by 3 inch glass microscope slide is a preferred solid support for the micro spot tests. These plates are relatively easy to handle and they contain a solid substance that fluoresces brightly when illuminated with short wavelength UV light. Therefore it is possible to detect substances that absorb UV light by "fluorescence quenching", as well as by other detection and visualization methods. A non-limiting list of suitable TLC strips which can be used in carrying out the invention include Diamond MK6F Silica Gel 60A TLC plates, Catalog No. 4500-100 from Whatman, Inc., Clifton N.J. 07014, which contains a 250 micron thick layer on a 1 by 3 inch glass microscope slide; Silica Gel HL, 250 micron thick layer, Cat. No. 46931, Analtech, Newark, Del. 19714; Silica Gel HLF, 250 micron layer, Cat. No. 47931, Analtech, Newark, Del. 19714; Ammonium Sulfate (5%) Modified Silica Gel H, 250 micron layer, Self Charring Plates, Cat. No. 74031 (without indicator) and Cat. No. 75031 (with fluorescent indicator); Silica Gel F-254 TLC media, plastic backed, layer thickness 0.25 mm, Cat #5775 from E. M. Laboratories, Elmsford, N.Y. 10523; Silica Gel F-254 TLC media, aluminum backed, layer thickness 0.2 mm, Cat #5539 from Alltech Associates, Deerfield, Ill. 60115; Silica Gel TLC media, plastic backed, layer thickness 100 microns, Product Number 13179, Cat. #4G 6801, Eastman Kodak Co., Rochester, N.Y. 14650; $C_{18}$/Silica Gel, 250 micron thick layer, Cat. No. 17021, Analtech, Newark, Del. 19714; $NH_2$/Silica Gel, 250 micron thick layer, Cat. No. 18021, Analtech, Newark, Del. 19714; CN/Silica Gel, 250 micro thick layer, Cat. No. 19021, Analtech, Newark, Del. 19714; Nano-SIL G High Performance Thin-Layer Chromatography (HPTLC) Plates, Catalog 81841, Alltech, Inc., Deerfield, Ill. 60015; Nano-SIL-NH2/V (Amino) Catalog No. 8100026, Alltech, Inc., Deerfield, Ill. 60015; Nano-SIL-CN/UV (Cyano) Catalog No. 8110022, Alltech, Inc., Deerfield, Ill. 60015; Reversed Phase Sil Gel 60, RP-2 (Dimethyl bonded) Cat. No. 5746, RP-8 (Octyl bonded) Cat. No. 15388-7, RP-18 (Octadecyl bonded) Cat. No. 15389-7, Alltech Inc., Deerfield, Ill. 60015; "hybrid plates" (one plate designed for both reverse-phase and normal phase TLC), Catalog Number 818144, Alltech, Inc., Deerfield, Ill. 60015; Avicel Microcrystalline Cellulose Uniplates, 250 micron thick layer, Cat. No. 05061 (without indicator) and Cat. No. 06061 (with fluorescent indicator), Analtech, Newark, Del. 19714; SILCEL-Mix 25 UV254, Catalog No. 810043, Alltech, Inc., Deerfield, Ill. 60015; ALOX-100 UV254, Catalog No. 807033, Alltech, Inc., Deerfield, Ill. 60015; GUR N-25 UV254, Catalog No. 810073, Alltech, Inc., Deerfeld, Ill. 60015; Nano-SIL C18-100 UV254, Catalog No. 811062, Alltech, Inc., Deerfield, Ill. 60015; SIL N-HR/UV254, Catalog No. 804023, Alltech, Inc., Deerfield, Ill. 60015; CEL 300 AC-30%, Catalog No. 801043, Alltech, Inc., Deerfield, Ill. 60015; CEL 300 DEAE, Catalog No. 801073, Alltech, Inc., Deerfield, Ill. 60015; Polyamide 6 UV254, Catalog No. 803023, Alltech, Inc., Deerfield, Ill. 60015; ALOX N/UV254, Catalog No. 802021, Alltech, Inc., Deerfield, Ill. 60015; Instant Thin Layer Chromatography Polysilicic Acid Gel Impregnated Glass Fiber Sheets with Fluorescent Indicator, Product Number 51435, Gelman Instruments, Ann Arbor, Mich. 48106; Instant Thin Layer Chromatography Sheets, Type SG, Product Number, 61886, Gelman Instrument Co., Ann Arbor, Mich. 48106; TLC Plates, Silica Gel 60 F-254, aluminum backed, layer thickness 0.2 mm, Product #37360, Catalog #Z19,329-1, Aldrich Chemical Co., Milwaukee, Wis. 53233; Silica Gel IB Flexible (plastic backed) Sheets for Thin Layer Chromatography, layer thickness 250 microns, Product Number 4462-02, J. T. Baker, Inc., Phillipsburg, N.J. 08865; Aluminum Oxide IB Flexible (plastic backed) Sheets for Thin Layer Chromatography, layer thickness 200 microns, Product Number 4466-00, J. T. Baker, Inc., Phillipsburg, N.J. 08865; Reversed Phase hydrocarbon impregnated) HPTLC Uniplates, 150 micron thick layer, Cat No. 54377 (without indicator) and Cat. No. 55377 (with fluorescent indicator), Analtech, Newark, Del. 19714; MKC18F Reversed Phase TLC plates, glass backed (1"×3" plates), layer thickness 200 microns, Cat. #4803-110 from Whatman, Inc., Clifton, N.J. 07014; H-RP2F (ethyl bonded silica gel) Reversed Phase TLC plates, layer thickness 150 microns, Cat. No. 08527, Analtech, Newark, Del. 19714; Polyram Ionex SA-NA Ion Exchange Resin and Silica Gel Mixed Layer on Plastic, Catalog Number M806013, Bodman Chemical Co., Aston, Pa. 19014; Polygram Ionex 25 SB-AC Ion Exchange Resin and Silica Gel Mixed Layer on Plastic, Catalog Number 806023, Bodman Chemical Co., Aston, Pa. 19014; and 2000 micron thickness Silica Gel G Preparative Uniplates, Catalog Number 01055, Analtech, Inc., Newark, Del. 19714. The composition of adsorbent coatings contained on the listed TLC plates include silica gel, high performance thin layer chromatography (HPTLC) silica gel, polysilicic acid, aluminum oxide, cellulose, polyamide, reversed phase silica Gel $C_2$ (dimethyl bonded), reversed phase silica gel $C_2$ (ethyl bonded), reversed phase silica gel $C_8$ (octyl bonded), reversed phase silica gel $C_{18}$ (octadecyl bonded), acetylated cellulose, silica gel modified with amino groups, silica gel modified with cyano groups, Kieselghur impregnated with hydrocarbons, anionic and cationic anion exchange resins, diethylaminoethyl cellulose, and mixtures of the listed sorbents.

If the thin-layer chromatography (or TLC) sheets or plates are those which are commercially available, they can be further scored into small sample areas within the sheet, i.e. ½ inch×½ inch or a similar size. The scoring of the plate reduces the likelihood that the liquid solutions applied in one spot test will creep into the sections reserved for other spot tests. Alternatively, the method can be carried out using TLC sheets that are specifically made to carry out the micro spot tests of the present invention.

Use of pre-deposited detector reagents on the sorbent coatings for microspot tests is described briefly in a Continuation-In-Part of U.S. application Ser. No. 08763,181 filed Dec. 11, 1996. An important aspect of this methodology is that the shelf-life stability of pre-deposited reagent or reagents on the sorbent coating is improved when the prepared medium for the microspot test is stored dry and preferably in an inert atmosphere.

The methodology involves (1) application of the detector reagent to a TLC plate preferably by applying a solution containing the detector reagent to a sorbent coated plate and allowing the solvent to evaporate, (2) thoroughly drying the predeposited reagent on the plate, and (3) storing the dry plate in a dry and inert atmosphere.

When the plate containing predeposited reagent(s) is used, the sample solution is applied to the sorbent media or TLC plate using a microcap. (In one variation of the methodology, which is described in detail below, the actual detector reagent for the test is prepared "in situ" by heating the plate to thermally decompose the original reagent predeposited on the plate). Two considerations include (a) preventing detector reagent washout from occurring when the sample solution is applied to the sorbent coating using a microcap, and (b) improving the stability of the predeposited detector reagent on the sorbent coating, particularly with regard to oxidation and hydrolysis.

The first consideration can be addressed by pre-depositing on the sorbent layer only detector reagents that are insoluble (or have very low solubility) in the solvent that is used to dissolve the analyte. It should be understood that the polarity of the detector reagent and the solvent selected for preparing the sample solution containing the analyte should preferably be near the opposite extremes of the polarity scale. For example, if the detector reagent is water soluble and, therefore, a highly polar compound, the solvent for the analyte should be hexane, or some other highly non-polar solvent. Furthermore, the polarity of the detector reagent and the sorbent material on which the detector reagent is pre-deposited should be similar. For example, if the detector reagent to that is to be predeposited on a TLC plate is highly polar, the sorbent material of the TLC plate should be silica gel, or some other highly polar sorbent.

The second consideration can be addressed in different ways. One way is to store the prepared plates in dry condition in an atmosphere that is free of moisture and in which air has been displaced by an inert gas such as nitrogen or argon, Another way is to vacuum-seal the prepared plates in an inert atmosphere such as nitrogen or argon.

Examples of highly polar detector reagents (along with examples of the analytes they detect in brackets) include:

ammonium cerium(IV)nitrate [polyalcohols]

ammonium cerium(IV)sulfate [alkaloids]

ammonium iron(III)sulfate [flavonoids, alkaloids]

bismuth chloride [sterols]

cerium(IV)sulfate [iodine compounds]

copper chloride [oximes]

hydrogen tetrachloroaurate [thiols, thiophosphonic acids, amines]

iron(III)chloride [phenol, hydtoxamic acids]

lead acetate basic [flavonoids]

lead(IV)acetate [compounds containing 1,2-diol groups]

palladium chloride [thiophosphate esters, organophosphorus insecticides]

potassium bismuth iodide [alkaloids, quaternary ammonium compounds, some amines]

potassium iodide plateate [alkaloids, ketosteroids, other compounds containing nitrogen]

silver nitrate [phenols]

zinc chloride [steroids sapogenins, steroids]

Gold chloride (hydrogen tetrachloroaurate tihydrate) when dry is hygroscopic and will become moist when the compound is exposed to air. Furthermore, some sorbents (for example, silica gel) when dry are hygroscopic and will also attract moisture from the air. If a silica gel sorbent that contains predeposited gold chloride is dried thoroughly and sealed in a dry and inert atmosphere, breaking the seal will result in moisture from air combining with the detector reagent. Moisture accumulated on the sorbent material and in the detector reagent in this way facilitates detection of EMPTA when gold chloride is the detector reagent predeposited on silica gel.

Other detection reactions, such as the detection of methanesulfonyl chloride or certain pesticides that are acetylating or phosphorylating agents using 1,3-diisonitrosoacetone quanidinium salt as the detector reagent, are also preferably performed using silica gel coated TLC plates because of the hygroscopic property of silica gel and the need for moisture to facilitate the detection reaction.

Furthermore, it is possible to generate reagents that are essential for or to improve the detection reactions in microspot tests "in situ" by thermally decomposing one or more of the predeposited reagents. A number of detection reactions proceed or are improved when a sufficient amount of acid, base, water (or a combination of acid and water or base and water) is present in the detector composition. An example of a detection reaction that is improved when water is present is the detection of methanesulfonyl chloride using 1,3-diisonitrosoacetone quanidinium salt as the detector reagent, and an example of a detection reaction that requires a strong base along with water is the detection of dimethylsulfate using 4-(4'-nitrobenzyl)pyridine as the detector reagent. An example of a detection reaction that requires a strong acid (sulfuric acid) is the detection of alkyloxy methylphosphonic acids using molybdenum oxide as the detector reagent.

Below are detector reagents that can be co-deposited on a sorbent coated plate along with other detector reagents, and then stored in a dry state in an inert atmosphere, and which can be thermally decomposed after application of the sample solution to produce an acid, base, or water for use in a detection reaction.

- ammonium bisulfate [produces sulfuric acid (a strong acid) as a result of thermal decomposition]
- ammonium sulfate [produces a sulfuric acid (a strong acid) as a result of thermal decomposition]
- sodium bicarbonate [produces a strong base (sodium carbonate) as a result of thermal decomposition]
- potassium bicarbonate [produces a strong base (potassium carbonate) as a result of thermal decomposition]
- magnesium sulfate heptahydrate [produces water as a result of thermal decomposition]
- magnesium sulfate decahydrate [produces water as a result of thermal decomposition]

Furthermore, other salts containing water of hydration can also be thermally decomposed at a various temperatures to produce the water needed in detection reactions.

For another aspect of this invention, where it is not possible to pre-deposit two or more reagents on a single sorbent coated plate due to incompatibility of the reagents or where it is desirable to detect the analyte using two distinct steps, each of the required reagents can be pre-deposited on a separate piece of material and the micro-spot test matrix can be combined as two layers. For example, when 4-(4'-nitrobenzyl)pyridine is used as the reagent for detecting alkylating agents such as dimethylsulfate or epichlorohydrin, the test is preferably performed in two separate steps. The first step involves the alkylation of 4-(4'-nitrobenzyl)pyridine and the second step involves basification of the alkylated 4-(4'-nitrobenzyl)pyridine to produce a blue product. The matrix for the micro-spot test would be constructed using two different media which would be combined as two layers in the final test item. One layer would contain 4-(4'-nitrobenzyl)pyridine pre-deposited and dried on a silica gel TLC medium such as Gelman Instant Thin Layer Chromatography Polysilicic Acid Impregnated Glass Fiber Sheets, Product Number 51435, Gelman Sciences, Ann Arbor, Mich. 48106. It is to this medium that the sample solution is to be applied using a micro-cap. The second layer would contain a strong base such as potassium carbonate or sodium hydroxide predeposited and thoroughly dried on a cellulose support such as Gelman Solvent Saturation Pads Product Number 51334, Gelman Sciences, Ann Arbor Mich. 48106 or Whatman Chromatography Paper Grade 17, Whatman Inc., Clifton, N.J. 07014). Once the alkylation step is performed, which may or may not require heat depending on the target analyte, the final step is performed by placing several drops of water (for example, using a dropping bottle such as Catalog Number 211620 from Wheaton, Inc., Millville, N.J. 08332) on the cellulose layer that contains the strong base. When the strong base dissolves in the water and the basic solution so formed comes in contact with and wets the layer containing alkylated 4-(4'-nitrobenzyl)pyridine, a blue color signifying a positive test is obtained.

Figure 7:
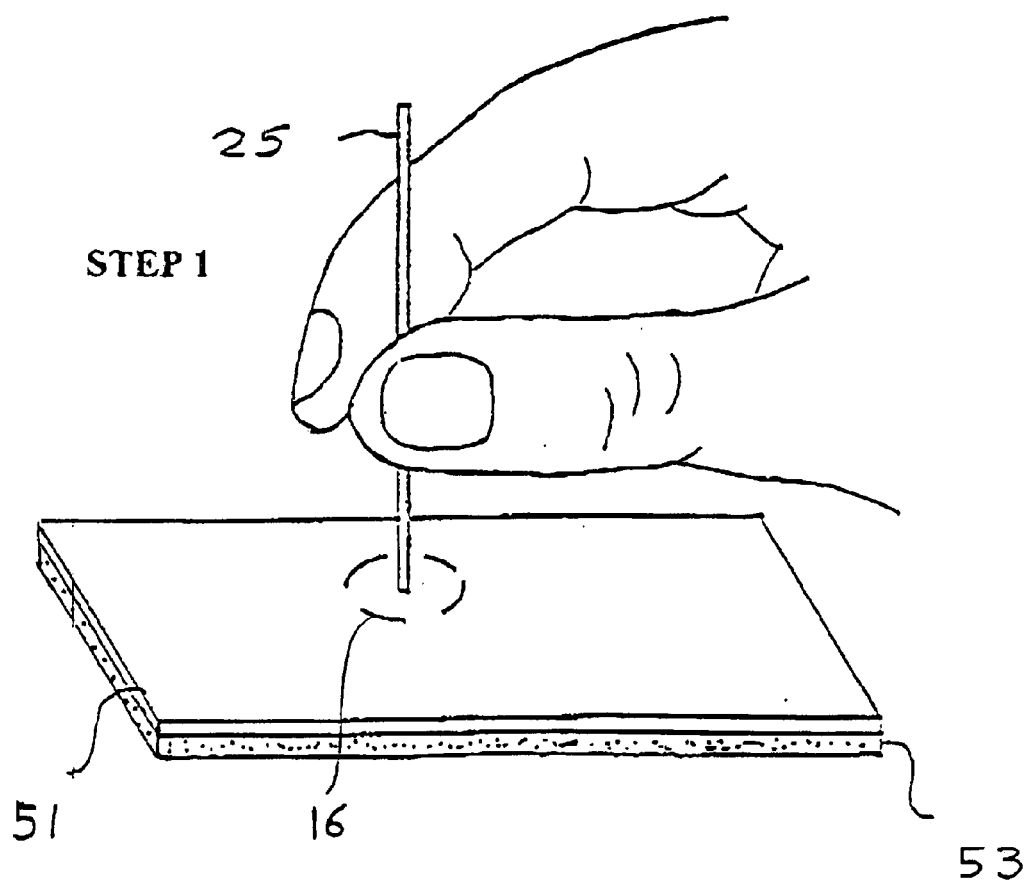
FIG. 7 is a view of a two layer microspot test.
Figure 8A:
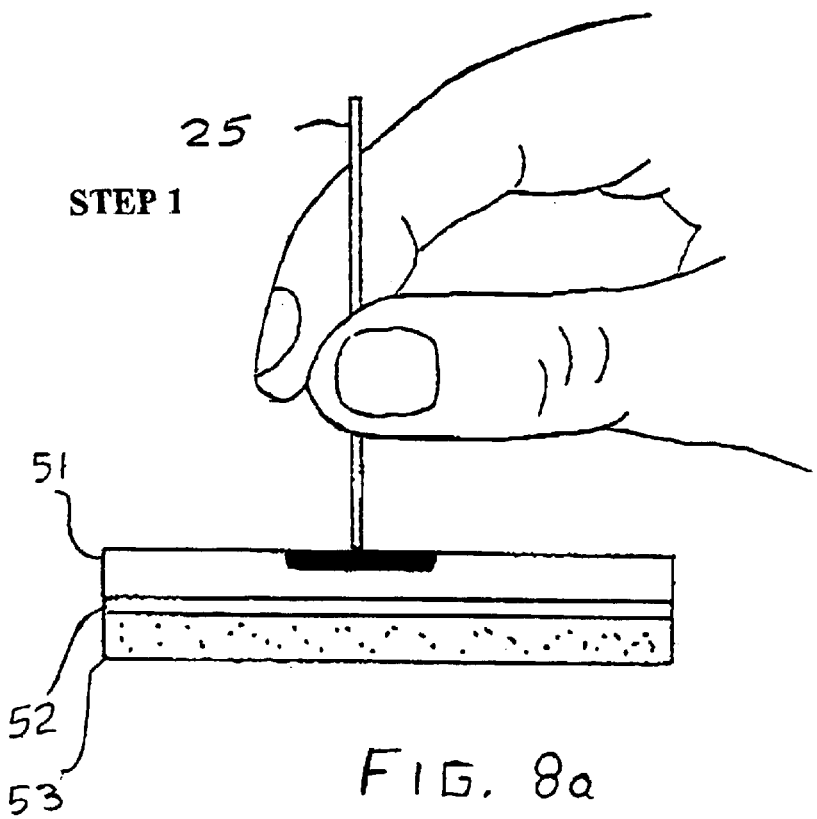
FIGS. 8a and 8b are an illustration of a two step method for detecting an analyte.
Figure 8B:
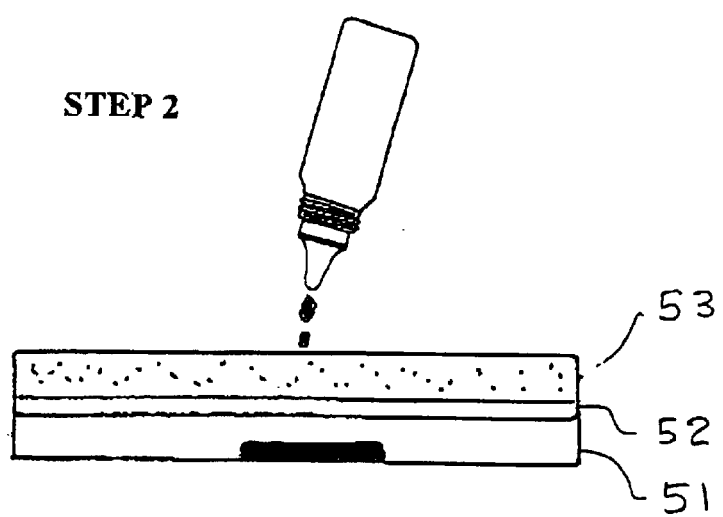

FIG. 7 is a view of a two layer plate, layers 51 and 53, used for a microspot test. FIG. 8a shows step 1 and FIG. 8b shows step 2 of the microspot test with two different layers of reagents. The top layer 51 could be Gelman Instant Thin Layer Chromatography Polysilicic Acid Impregnated Glass Fiber Sheets Product Number 51435, Gelman Sciences, Ann Arbor, Mich. 48106. However, any sorbent, including those disclosed in U.S. Pat. No. 4,301,027 assigned to Dynamit Nobel AG and a divisional patent, U.S. Pat. No. 4,436,823 assigned to Dragerwerk Aktiengesellschaft and U.S. Pat. No. 5,308,495 and U.S. Pat. No. 5,824,526 could be impregnated on glass fiber paper and used instead. The top layer can also be a DE-81 (diethylaminoethyl ion exchange paper, 3.5 microequivalents per cm) paper (DEAE) which is described in U.S. Pat. No. 4,324,858. Furthermore the top layer could also consist of glass fiber paper impregnated with any of a variety of sorbents that are used to pack high performance liquid chromatography columns, or with sorbents scraped from TLC plates. It is important that the support containing the sorbent that is used as the top layer is a porous material. When a porous material is used, the second reagent, which dissolves in water added in step 2, is able to reach the analyte. The second layer 53 is preferably a thick cellulose paper such as Gelman Solvent Saturation Pads (Product Number 51334, Gelman Sciences, Ann Arbor, Mich. 48106 or Whatman #17 Chromatograph Paper Grade 17, Whatman, Inc., Clifton, N.J. A thick glass fiber paper or quartz fiber paper can also be used as the second layer. The dotted lines 16 in FIG. 7 represent the location where a reagent would be predeposited on Gelman Instant Thin Layer Chromatography Polysilicic Acid Impregnated Glass Fiber Sheet, which has properties similar to a silica gel TLC plate.

Some of the reagent combinations that could be used when the test is conducted in two layers, where layer 51 is layer A and layer 53 is layer B, include:

| Reagent in Layer A | Reagent in Layer B | Analyte Detected |
| --- | --- | --- |
| 4-(4'-nitrobenzyl)pyridine | potassium carbonate | dimethyl sulfate epichlorohydrin alkylating agents |
| Heat (ca. 90° C. for 2 minutes) should be used after step 1. | | |
| (4'-nitrobenzyl)pyridine | sodium hydroxide | same analytes as above |
| Heat (ca. 90° C. for 2 minutes) should be used after step 1. | | |
| gold chloride (hydrogen tetrachloroaurate (III) trihydrate) | sodium hydroxide | thiols phosphono-thioic acids thioethers |
| Step 2 should be performed two minutes after step 1. | | |
| eel cholinesterase | indoxyl acetate | cholinesterase inhibitors |
| Step 2 should be performed several minutes after step 1. | | |
| cholinesterase | 2,6-dichloroindo-phenyl acetate | cholinesterase inhibitors |
| Step 2 should be performed several minutes after step 1. | | |

It is possible that other reagent combinations that are listed in Table 1 contained in Continuation-In-Part of U.S. application Ser. No. 08/763,181, filed Dec. 11, 1996 could also be used.

FIGS. 8a and 8b show both step 1 and step 2 where a piece filter paper 52, such as Whatman #1 filter paper, is placed between the two layers. This would insure that the two reagents did not come in contact with each other prematurely (in storage, for example).

Figure 9:
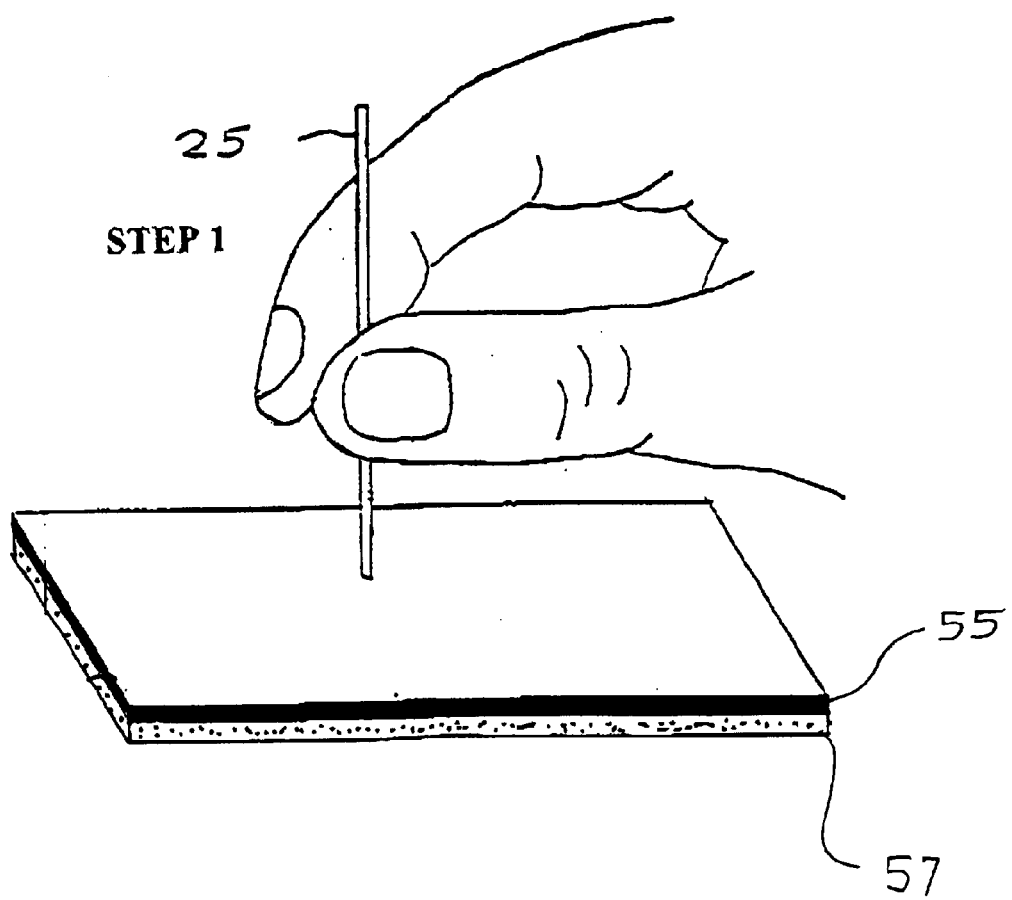
FIG. 9 is a view of a two layer plate having a uniform impregnated detector reagent.

FIG. 9 shows a two layer plate where the top layer 55 contains a uniform distribution of the detector reagent as would be the case if glass fiber paper were impregnated with the detector reagent insolublized or trapped in the sorbent if the Dragerwerks Patents or the Gel-sol patents were used to prepare the sorbent containing detector reagent. Also shown is a lower layer 57.

Figure 10A:
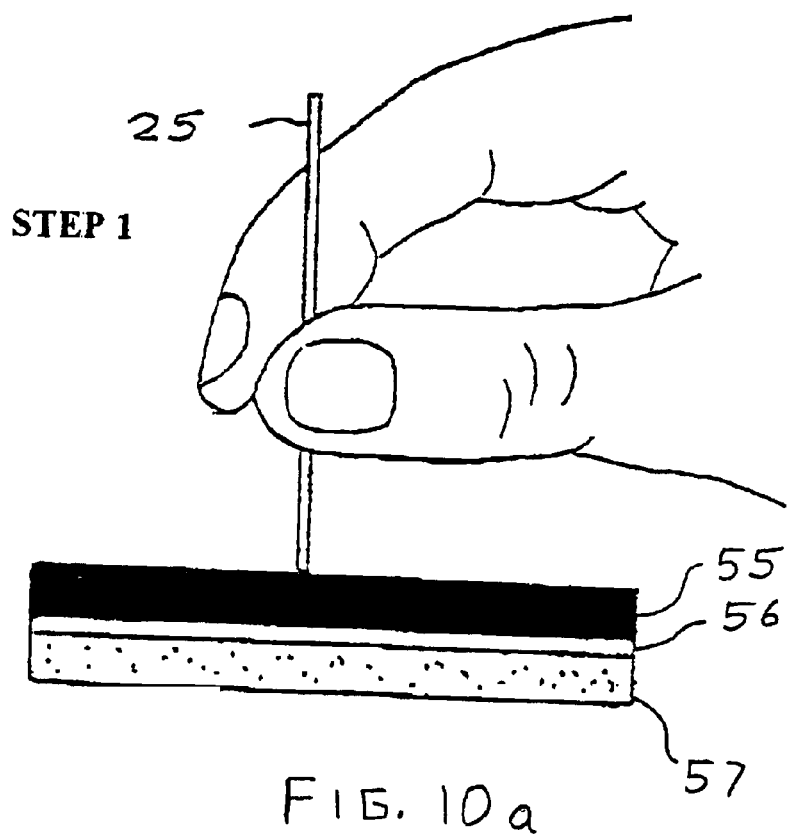
FIGS. 10a and 10b are an illustration of a two step method for detecting an analyte with the two layer plate of FIG. 9.
Figure 10B:
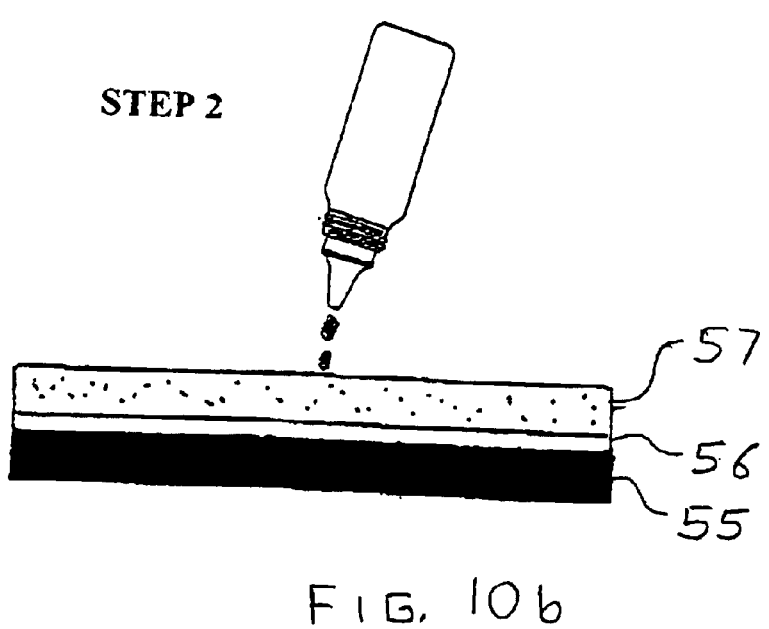

FIGS. 10a and 10b show the two steps of the microspot test where layer 55 contains a glass fiber impregnated with an insolublized or entrapped detector reagents prepared according to the Dragerwerks patents or the Gel Sol patents. A layer of material 56 may be positioned between layer 55 and 57.

Due to the convenience of using dry and insoluble detector reagents in chemical detection tests, and the knowledge that a large number of detector reagents are soluble in many solvents, methodology has been developed for preparing a dried silica gel containing a detector reagent in insolubilized form. The methodology for preparing silica gels containing such insolublized detector reagents which remain reactive is described in U.S. Pat. No. 4,301,027 assigned to Dynamit Nobel AG and U.S. Pat. No. 4,436,823 assigned to Dragerwerk Aktiengesellschaft. Silica gels containing insolublized detector reagents prepared using the methodology described in these patents can be used in the micro-spot tests. Furthermore, U.S. Pat. No. 5,308,495 and U.S. Pat. No. 5,824,526 contain methodology for preparing sol-gel glasses containing entrapped colorimetric reagents which can be coated on a solid support and used as the medium for microspot tests.

Examples of normally soluble chromogenic detector reagents that can be insolublized on silica gel using the methodology described in U.S. Pat. No. 4,301,027 and U.S. Pat. No. 4,436,823 or can be incorporated into sol-gel glasses using the methodology described in U.S. Pat. No. 5,308,495 and U.S. Pat. No. 5,824,526 include cholinesterase, eel cholinesterase, bromcresol green; 7,7,8,8-tetracyanoquinodimethane (TCNQ); gold chloride, potassium bismuth iodide; 1,3-diisonitrosoacetone guanidinium salt; bis(diethylamino)benzophenone oxime; bis(diethylamino)benzophenone; bis(dimethylamino) thiobenzophenone; phenylazoformic acid 2-diphenythydrazide; diphenylcarbazone; diphenylthiocarbazone; mercuric salt; diethyldithiocarbamic acid silver salt; 2, 2'-dithiobis(5-nitropyridine); 5,5-dithiobis(2-nitrobenzoic acid) i.e., Ellman's Reagent; and ammonium molybdate. Below is a non-limiting partial list of other detector reagents that can be used in the methodology described herein. Other detector normally soluble detector reagents that are also applicable are contained in references 1–42 which are incorporated herein by reference.

Table 1 is a partial list of detector reagents and the target analytes which are detected by the reagents.

TABLE 1

Partial List of Detector Reagents for Microspot Tests

| Detector Reagent | Target Analytes |
|---|---|
| alizarin | cations |
| aluminum chloride | flavonoids |
| 4-aminohippuric acid | reducing sugars |
| ammonia | tetracyclines |
| ammonium cerium(IV)nitrate | polyalcohols |
| ammonium cerium(IV)sulfate | alkaloids |
| ammonium iron(III)sulfate | flavonoids |
| ammonium iron(III)sulfate | alkaloids |
| aniline/phosphoric acid | sugars |
| aniline phthalate | reducing sugars, anions of halogen oxyacids |
| p-anisaldehyde | reducing sugars |
| p-anisidine phthalate | reducing sugars |
| anthrone | ketoses |
| antimony(III)chloride | flavonoids |
| antimony(III)chloride | vitamin A and D, carotenoids, steroids, sapogenins, steroid glycosides, terpenes, resins, steroid sapogenins |
| aurin tricarboxylic acid (aluminon) | aluminum ions, chromium ions, lithium ions |
| bismuth chloride | sterols |
| bromocresol green (or bromcresol green) | organic and inorganic acids, |
| bromcresol purple | dicarboxylic acids, halogen ions |
| cacotheline | vitamin C |
| carmine | polysaccharides |
| cerium(IV)sulfate | organic and inorganic iodine compounds |
| chloramime-T | caffeine |
| 1-chloro-2,4-dinitrobenzene | nicotinic acid, nicotinamide, pyridoxol |
| chromosulfuric acid | organic compounds |
| chromotropic acid | methylenedioxyphenyl-type compounds nicotine, hydrastine, sesamine |
| cobalt(II)chloride | organic phosphate esters |
| cobalt(II)thiocyanate | alkaloids, amines |
| copper chloride | oximes |
| alpha-cyclodextrin | straight-chain lipids |
| 3,5-diaminobenzoic acid/ phosphoric acid | 2-deoxy-sugars |
| o-dianisidine | aldehydes, ketones |
| 2,6-dibromoquinone chlorimide | phenols |
| 2',7'-dichlorofluorescein (fluorogenic indicator) | saturated and unsaturated lipids |
| 2,6-dichlorophenolindophenol sodium salt | organic acids, keto acids, vitamin C |
| 2,6-dichloroquinone chlorimide | antioxidants, adrenaline and derivatives, cyanamide and derivatives |
| dicobalt octacarbonyl | acetylene compounds |
| diethyl malonate | 3,5-dinitrobenzoic acid esters |
| dimethylaminobenzylidenerhodanine | silver ions, copper ions, mercury ions |
| 4-dimethylaminocinnamaldehyde | indoles |
| dimethyl-p-phenylenediamine dihydrochloride | peroxides |
| 1,3-dinitrobenzene | 17-ketosteroids |
| 3,5-dinitrobenzoic acid | cardiac glycosides |
| 3,5-dinitrobenzoic acid | reducing sugars |
| 2,4-dinitrofluorobenzene | amino acids |
| 2,4-dinitrophenylhydrazine | free aldehyde groups, free keto groups, ketoses |
| 3,5-dinitrosalicylic acid | reducing sugars |
| diphenylamine | glycolipids |
| diphenylboric acid-beta-aminoethyl ester | alpha and gamma-pyrones |
| diphenylcarbazide | silver ions, lead ions, mercury ions, copper ions, tin ions, zinc ions, calcium ions |
| diphenylcarbazone | addition compounds of unsaturated fatty acids |
| diphenylcarbazone | cations |
| diphenylpicrylhydrazyl | essential oils |
| 2,5-diphenyl-3-(4-styrylphenyl)-tetrazolium chloride | reducing steroids, corticosteroids |
| dipicrylamine | choline, vitamin B1 |
| dithizone | ions of heavy metals |
| 4,4'-dithiodianils | thiols |
| ethylenediamine | catechol amines |
| Fast blue salt B | phenols, coupling amines |
| fluorescein | lipids |
| glyoxalbis(2-hydroxyanil) | cations |
| hydrazine sulfate | piperonal, vanillin, ethyl vanillin |
| hydrochloric acid | glycals |
| hydrogen peroxide | aromatic acids |
| 8-hydroxyquinoline | barium ions, strontium ions, calcium ions |
| indandione | carotenoid aldehydes |
| iodine | general detection reagent |

TABLE 1-continued

Partial List of Detector Reagents for Microspot Tests

| Detector Reagent | Target Analytes |
|---|---|
| iron(II)thiocyanate | peroxides |
| isonicotinic acid hydrazide | ketosteroids |
| lead acetate (basic) | flavonoids |
| lead(IV)acetate | 1,2-diol groups |
| magnesium acetate | anthraquinone glycosides |
| mercury(I)nitrate | barbiturates |
| methylene blue | sulfate esters of steroids |
| methylunmbelliferone (fluorogenic detector reagent) | heterocyclic compounds containing nitrogen |
| methyl yellow | chlorinated insecticides |
| molybdatophosphoric acid | reducing compounds, lipids, sterols, steroids |
| morin | aluminum ions |
| 1-naphthol/hypobromite | guanidine derivatives |
| naphthoquinone-sulfonic acid sodium salt | amino acids, aromatic amines |
| 1-naphthylamine | 3,5-nitrobenzoic acid esters, dinitrobenzamides |
| ninhydrin | amino acids, amines, amino-sugars, iron ions |
| 2-nitroso-1-naphthol-4-sulfonic acid | |
| palladium(II)chloride | thiophosphate esters, organophosphorus insecticides |
| phenol/sulfuric acid | sugars |
| m-phenylenediamine | reducing sugars |
| phenylfluorone | germanium |
| phenylhydrazine | dehydroascorbic acid |
| phosphoric acid | sterols, steroids |
| potassium hexacyanoferrate(II) | iron(III) ions |
| potassium hexacyanoferrate(III) | adrenaline and derivatives |
| potassium hexacyanoferrate(III) | vitamin B1 |
| potassium hexacyanoferrate(III)/ potassium hexacyanoferrate(II) | morphine |
| methanol potassium hydroxide | coumarins, anthraquinone glycosides |
| potassium iodine plateate | alkaloids, other organic compounds containing nitrogen, ketosteroids |
| potassium permanganate (neutral) | easily oxidizable compounds |
| quinalizarin | cations |
| p-quinone | ethanolamine |
| rhodamine 6G | lipids |
| rhodanine | carotenoid aldehydes |
| rhodizonic acid sodium salt | barium ions, strontium ions |
| rubeanic acid | lead ions, cobalt ions, copper ions manganese ions, nickel ions, mercury ions, bismuth ions |
| silver nitrate | phenols |
| sodium meta-periodate | hydroxyamino acids serine, threonine |
| sodium meta-periodate/ 4-nitroaniline | deoxy-sugars |
| sodium nitroprusside | compounds with sulfhydryl group |
| sodium pentacyanoamino ferrate(II) | urea, thiourea, guanidines |
| sodium tetraphenylboron | alkaloids |
| starch | amylases |
| sulfuric acid | general visualization reagent |
| tetracyanoethylene | aromatic hydrocarbons, phenols, heterocyclic compounds |
| tetranitrodiphenyl | cardiac glycosides |
| tetraphenyldiboroxide | flavones |
| tetrazolium blue | corticosteroids, reducing compounds |
| thiobarbituric acid | sorbic acid |
| thymol blue | dimethylamino acids |
| tin(IV) chloride | triterpenes, sterols, steroids, phenols, polyphenols |
| titan yellow | cadmium ions |
| p-toluenesulfonic acid | steroids, flavonoids, catechins |
| o-tolidine (fluorogenic detector reagent) | chlorinated insecticides |
| toluidine blue | acidic polysaccharides |
| trichloroacetic acid | steroids, digitalis glycosides, Veratrum alkaloids, vitamin D |
| N,2,6-trichloro-p-benzoquinone-imine | thiophosphate pesticides |
| 2,4,6-trinitrobenzoic acid | cardiac glycosides |
| 2,3,5-tripheyltetrazolium chloride | reducing sugars, corticosteroids, reducing compounds |
| tungstophosphoric acid | reducing compounds, lipids, sterols, steroids |
| violuric acid | alkali and alkaline earth metal ions |
| xanthydrol | tryptophan, indole derivatives |
| zinc chloride | steroid sapogenins, steroids |
| zinc uranyl acetate | sodium ions |

It is generally expected that a small amount of the detector reagent in solution, such as single drop, that is pre-deposited in the sorbent material will be sufficient in order to produce a result. In some tests heat can be used to accelerate the reaction of a detector reagent with the analyte. If the test is positive, in most cases a small spot within the reagent spot on the TLC sheet changes color, or changes fluorescence under UV illumination, within 5 minutes. Since the level of analyte tends to be directly related to the size of the color change within the spot, some quantification of the analyte levels may be possible. It is also possible to detect an analyte where the detection signal produced with the disclosed methodologies is a change in the intensity of color rather than an actual color change. For example, strong bases can be detected with the micro spot test of the present invention where Bromcresol Green is the detector reagent. The detection signal that was produced was a small dark blue spot within a light blue spot in the test with Bromcresol Green when the analyte was a strong base.

FIG. 6 is a plan view of a sorbent layer depicting how the results of a microspot test may appear after a microcapillary tube has been added to the surface of a sorbent layer containing a reagent. The two circular spots or regions 40 and 42 are generally representative of where the detector reagent has been added to a sorbent layer and then allowed to dry. Subsequently, a solution containing the analyte is deposited onto the surface of the sorbent layer with a microcapillary tube. The spot 40, on the left, represents the results when a negative result is produced (no analyte is present) and the spot 42, on the right, represents the results when a positive result is produced (an analyte is present, producing a chromogenic indication). The right spot is shown to contain a smaller spot or point 43 in the center of the detector reagent spot to represent that the unknown has been localized about the point where the microcapillary tube contacts the sorbent material. While there may be some expansion of the spot relative to the size of the opening, such as would occur with a relatively high concentration of analyte or use of different solvents, the analyte generally remains concentrated at the identified spot of deposition.

It was found that high detection sensitivity is attained with the disclosed methodology where the analyte is dissolved in a solvent and then applied in small amounts to a thin-layer chromatography media by capillary action using a microcapillary tube. Thus, the test method of the present invention is referred to as micro spot tests due to the minute quantities of analyte that are capable of being detected. It is further believed that the increased sensitivity of the micro spot tests is due at least in part to the fact that the analyte remains concentrated and localized at the spot of deposition.

The micro spot test method is generally solvent dependent, at least with respect to the solvents for the analyte. In general, the solvent for target analytes should be selected so that the analytes are concentrated in a small spot when the solution containing the analytes is applied to a TLC plate with a microcapillary tube. For example, sorbents formed of silica gel and aluminum oxide (alumina) for TLC plates are normally polar compositions. When an analyte solution is applied to a polar sorbent coating, such as silica gel or alumina, with a microcapillary tube, a smaller and more compact spot will tend to form when the solvent for dissolving the analyte is closer to the low polarity end of the polarity scale. A low polarity or less polar solvent for the analyte can be a solvent selected from the group that includes ethylene dichloride, dichloromethane, ethyl ether, o-dichlorobenzene, chlorobenzene, benzene, o-xylene, m-xylene, p-xylene, methyl tertiary-butyl ether, toluene, carbon tetrachloride, trichloroethylene, n-butyl chloride, hexadecane, nonane, cyclohexane, trimethylpentane, petroleum ether, iso-hexanes, hexane, heptane, cyclopentane, trichlorotrifluoroethane, and pentane. Preferably, the solvent for a polar sorbent material such as silica gel will be selected from the group of hexadecane, nonane, cyclohexane, trimethylpentane, petroleum ether, iso-hexanes, hexane, heptane, cyclopentane, trichlorotrifluoroethane, and pentane.

Depending upon the sorbent material, suitable solvents for placing or pre-depositing the detector reagent in the sorbent material include acetic acid, water, aqueous buffer solution with a pH in the range 2–12, dimethylsulfoxide, N-methylpyrrolidone, N,N-dimethyl acetamide, N,N-dimethyl formamide, propylene carbonate, acetonitrile, 2-methoxyethanol, diethylcarbonate, pyridine, methanol, acetone, ethanol, 2-ethoxyethanol, dioxane, methyl ethyl ketone, methyl n-propyl ketone, methyl acetate, methyl isobutyl ketone, chloroform, tetrahydrofuran, n-propanol, methyl isoamyl ketone, ethyl acetate, 2-methoxyethylacetate, isobutyl alcohol, n-butyl acetate, 2-butanol, 2-propanol, 1-butanol, ethylene dichloride, dichloromethane, ethyl ether, o-dichlorobenzene, chlorobenzene, benzene, o-xylene, m-xylene, p-xylene, methyl tertiary-butyl ether, toluene, carbon tetrachloride, trichloroethylene, n-butyl chloride, hexadecane, nonane, cyclohexane, trimethylpentane, petroleum ether, iso-hexanes, hexane, heptane, cyclopentane, trichlorotrifluoroethane, and pentane. For polar sorbent materials, such as silica gel, the solvent for the detector reagent can be selected from the group of water, methanol acetone, and an aqueous buffer solution with a pH in the range 2–12 (to include buffers contained in U.S. Pat. No. 4,324,858 that describes stabilization of cholinesterase).

An exception two-layer microspot test exists when cholinesterase or eel cholinesterase are the detector reagents impregnated on DE-81 (diethylaminoethyl ion exchange paper) (DEAE paper) or other porous solid supports in combination with the methodology described in U.S. Pat. No. 4,324,858 assigned to Midwest Research Institute and is used at top layer. The bottom layer consists of indoxyl acetate or a substrate composition on a porous material prepared according to U.S. Pat. No. 4,324,858. In this exception the solvent for applying the analyte with a microcapillary tube to the enzyme composition on the top layer are preferably hexane (a non-polar solvent) or water (a polar solvent). A positive test is a white spot in a blue background or lack of blue color in the top layer after the required reaction period with the substrate.

Attractive advantages of applying the detector regent to a TLC plate prior to applying the solutions containing the analyte(s) include (a) the liquid detector reagent solutions do not need to be prepared just prior to the test, (b) the required detector reagents can be pre-deposited at different locations on the same TLC media prior to on-site testing, and (c), the actual on-site testing steps are reduced to microcapillary deposition of solutions containing the analytes and visual observation of the results.

Additional attractive advantages realized by using sorbent coated plates made with silica gel containing insolubilized detector reagents, or sol-gels containing entrapped detector reagents are: (a) effectively addresses the concern arising from the possibility of washout of normally soluble detector reagent when the sample solution is applied to the sorbent coated plate, (b) permits the use of normally soluble detector reagents in an insolubilized form in silica gel, which is the preferred sorbent for many different microspot tests, (c) utilizes only the amount of detector reagent actually required for the test, and hence, eliminates excess liquid reagent disposal concerns and (d) good shelf-life stability of the packaged microspot test detector item is attainable by thoroughly drying the detector reagent/sorbent coating and storing the test medium in an inert atmosphere or vacuum sealing the dry reagent impregnated sorbent coated plate in a plastic film where the plate is contained in a dry, inert atmosphere.

Most of the analytes that are separated and then detected using thin layer chromatography (TLC) or paper chromatography (PC), including, but not limited to, those detected using either a chromogenic or fluorogenic visualization reagent (often referred to as TLC or PC spray reagent), should be capable of being detected with high detection sensitivity using the micro spot test methodology described herein.

An illustrative methodology of carrying out the methods of the present invention is provided below:

A sample suspected of containing the analyte ethyl methylphosphonothioic acid (EMPTA) is prepared by forming a hexane eluate from a polyester wipe. A microcapillary tube is used to draw up about 1 microliter of a solution containing the analyte and the end of the capillary tube is touched to a piece of a chromatographic sorbent medium, such as a TLC plate or medium, where gold chloride reagent has been previously deposited. The analyte solution wets the sorbent layer by capillary action. This caused a small brown spot to be produced within a background of a large yellow spot. This indicates that the EMPTA has been retained near the spotting point due to its strong interaction with the chromatographic sorbent material. Since the analyte collects in a small area near the spotting point as a result of capillary action and being adsorbed into the TLC media, it is possible to detect minute quantities of the analyte. When the technique is used of bringing a microcapillary tube into contact with the surface of a TLC media, the analyte solution will exit from the microcapillary tube by capillary action. If the microcapillary tube is not kept in contact with the surface of the chromatographic media, a droplet larger than the diameter of the microcapillary tube may form. When a droplet larger than the diameter of the microcapillary tube forms and then comes in contact with the thin layer chromatographic media, the solution will wet a larger area and the analyte will not be as concentrated in a compact spot. Consequently, the detection sensitivity of the test may be poorer.

The following non-limiting examples serve to illustrate this invention.

EXAMPLE 1

Microspot Test for O-Ethyl methylphosphonothioic Acid Using Gold Chloride Predeposited and Dried on a Sorbent-Coated Plate Detection Principle A brown spot in a yellow background signifies a positive test. This color change occurs at the location where the sample was spotted on the TLC plate. The intensity of the spot signifying a positive test increases with time or with addition of aqueous 2N sodium hydroxide solution. (After addition of 2 N sodium hydroxide the brown spot becomes black and the background color changes to gray).

Detector Reagents

1. Gold Chloride (deposited an aqueous 4% hydrogen tetrachloroaurate trihydrate solution on the sorbent coated plate and allowed the plate to dry prior to the test).
2. Aqueous 2N Sodium Hydroxide (optional—for use in step 2 of the test procedure).

PROCEDURE FOR PREPARING THE DETECTOR REAGENTS

Reagent #1

Place hydrogen tetrachloroaurate trihydrate (1g) in a 25 ml volumetric flask and add water to the mark. Place 2 ml of the solution in a 2-ml plastic dropping bottle. (One drop of this reagent solution is deposited on the TLC plate and the plate is then dried).

Reagent #2

Place sodium hydroxide (8.0 grams) in a 100 ml volumetric flask. Add approximately 75 ml of water and swirl until the sodium hydroxide dissolves. Allow the solution to cool to room temperature. Add water to the mark.

SOLVENT FOR THE ANALYTE: Hexane

PREFERRED SOLID SUPPORT: MK6F Silica Gel 60A Glass Backed TLC Plates, Cat. No. 4861-110, Whatman, Inc.

Analytes Detected with this Test

Ethyl methylphosphonothioic Acid (EMPTA). Also, compounds containing a thioether, thiophosphonic acid, or a sulfhydryl group.

EXAMPLE 2

Two Layer Microspot Test for Alkylating Agents Using 4-(4'Nitrobenzyl)pyridine in Combination with Potassium Carbonate Detection Principle In this two layer microspot test, two detector reagents are used in combination. The reagent in the top layer is 4-(4'-nitrobenzyl)pyridine. The reagent in the bottom layer is potassium carbonate. Depending on the target analyte, heat may or may not be necessary to insure reaction of the detector reagent in the top layer with the analyte. Heat accelerates the alkylation of 4-(4'-nitrobenzyl)pyridine by the analyte. Basification with aqueous potassium carbonate solution produced by adding several drops of water to the bottom layer results in a deprotonation reaction that produces a blue dye. A positive test response is a small dark blue or purple spot on a white or pale red background.

Detector Reagents

The top layer contains 4-(4'-nitrobenzyl)pyridine.

The bottom layer contains potassium carbonate.

Preparation of Top and Bottom Layer

Top Layer—place 4-(4'-nitrobenzyl)pyridine (20 mg) in a dropping bottle. Add 1 ml of acetone or methanol and swirl to dissolve the reagent. Add a drop of the solution to a 1 inch×½ inch piece of Gelman Instant Thin Layer Chromatographic Polysilicic Acid Impregnated Glass Fiber Paper and allow the solvent to evaporate. Bottom Layer—place potassium carbonate (300 mg) in a dropping bottle. Add 1 ml of water and swirl until the reagent dissolves. Add the solution dropwise to a 1 inch×½ inch piece of Gelman Solvent Saturation Pad and allow the solvent to evaporate. Dry both layers thoroughly. After the top layer and the bottom layer are dried thoroughly they are placed together and fastened at each end with a piece of cellophane tape.

SOLVENT FOR THE ANALYTE—hexane

ANALYTES DETECTED WITH THIS TEST-Epichlorohydrin, dimethylsulfate and alkylating agents in general.

PROCEDURE

1. Lock a 1-microliter microcap in the tip of locking forceps.
2. Place tip of microcap in a sample containing the analyte dissolved in hexane and wait a few seconds for the solvent to be drawn by capillary action to fill the microcap.
3. Place the tip of the microcap in contact with the surface of the top layer near the center of the location where the 4-(4'-nitrobenzyl)pyridine was deposited.
4. Heat the detector item at 90° C. for two minutes.
5. Turn the test item so the bottom layer is facing up.
6. Add water dropwise to the surface of the bottom layer until both the bottom layer and the top layer become wet.
7. Observe the top layer for the appearance of a positive test. A positive test is indicated by the appearance of a blue or purple spot in a white or pale red background. A positive detection signal appears within 1 minute.

While this micro spot methodology has particular application to the detection of chemical warfare agents and examples of such applicability are given to demonstrate such applicability, the methodology is likewise applicable for use in conjunction with or in place of other tests for environmental pollutants, contaminants, and hazards. Table 2 contains a list of compounds that are representative of the Priority 1 Analytes that can be detected with the processes of the present invention. This list represents a number of analytes that might be expected to be found during an on-site chemical weapons verification inspection. It will be understood by those of ordinary skill in the art that those analytes not specifically mentioned but known are also included herein and that the analyses for these analytes would be handled by the same methodology as analytes that are listed.

TABLE 2

PRIORITY 1 ANALYTES

| COMPOUND | SYNONYM |
| --- | --- |
| ethyl N,N-dimethylphosphoramidocyanate | GA |
| Isopropyl methylphosphonofluoridate | GB |
| Pinacolyl methytphosphonofluoridate | GD |
| Cyclohexyl methylphosphonofluoridate | GF |
| O-ethyl S-(2-diisopropylamino)ethyl methylphosphonothiolate | VX |
| bis(2-chloroethyl)sulfide | HD |
| bis[2-2-chloroethylthio)ethyl]ether | T |
| 2-chlorovinyldichloroarsine | L |
| Methylphosphonic difluoride | DF |
| ethyl-2-(diisopropylamino)ethyl methylphosphonite | QL |
| Isopropyl methylphosphonic acid | IMPA |
| Pinacolyl methylphosphonic acid | PMPA |
| Cyclohexyl methylphosphonic acid | CMPA |
| Methylphosphonofluoridic acid | MPFA |
| Methylphosphonic dichloride | DC |

TABLE 2-continued

PRIORITY 1 ANALYTES

| COMPOUND | SYNONYM |
| --- | --- |
| S-2-diisopropylamino)ethyl methylphosphonothioic acid | EA 2192 |
| ethyl methylphosphonic acid | EMPA |
| O-ethyl methylphosphonothioic acid | EMPTA |
| 1,4-dithiane | DITHIANE |
| 2-chlorovinylarsenious oxide | L-OXIDE |
| Methylphosphonic acid | MPA |

According to another aspect of the invention, there is provided a method whereby a more specific indication of the analytes can be achieved by using two or more micro spot tests in combination. By using a series of spot tests, the user is able to accumulate evidence for or against the presence of a Priority 1 Analyte in the sample without actually identifying any of the specific chemical components of the sample. This is important because the acceptance of the on-site screening procedures by the chemical industry may ultimately depend on methodologies that minimize or eliminate the need for unnecessarily subjecting chemical samples to sophisticated, and potentially more intrusive, analytical methods.

If a sample unknown gives positive tests for one or more Priority 1 Analyte, TLCs could be used to determine if the suspect sample is a mixture, and to obtain $R_f$ value(s) of the suspect analyte(s). For example, the TLC can be used to show the relative positions (from which $R_f$ values are obtained) for spots resulting from, for example, phosphonic acids and dithiane. The data can be obtained using a procedure similar to that developed by Sass and Ludemann for the separation of phosphonic acids, see J. of Chromatography, 187, 447–452 (1980), the contents of which are incorporated herein by reference. It is also noteworthy to mention that the shape of a spot on the TLC media and the rate at which the spot becomes colored in the presence of iodine vapor also helps to indicate which analyte is present. For example, a characteristic of the EMPTA spot is that it produces spots that have a long tail, Another characteristic of the EMPTA spot is that it changes color, going rapidly from colorless to brown when the TLC media is exposed to iodine vapor. While the micro spot test data may not be sufficient to identify the components of the unknown sample (which nonetheless is a desirable feature for screening tests), it is clear that the methods of the present invention can provide a considerable amount of evidence for the presence (or absence) of Priority 1 Analytes in a suspect sample.

Table 3 contains data that exemplify how three of the micro spot tests can be used in combination to accumulate presumptive evidence for the presence of several different Priority 1 Analytes. The sample unknown for the micro spot tests is one that would contain one of the following Priority 1 Analytes: MPA, EMPA, IMPA, PMPA, EMPTA and dithiane. For example, the data in Table 3 indicates that the response patterns from the three different spot tests can be used to distinguish dithiane and EMPTA from each other, and from MPA and several alkyloxy methylphosphonic acids that are also Priority 1 Analytes. A positive test result with the Bromcresol Green Test indicates that an acidic analyte, which could be MPA, or alkyloxy methylphosphonic acid, is in the sample. If the positive test with Bromcresol Green is combined with positive tests with TCNQ (7,7,8,8-tetracyanoquinodimethane) and gold chloride/NaOH, the response pattern could indicate that EMPTA may be present, but not dithiane, MPA or the alkyloxy methylphosphonic acids. A positive test with Bromcresol Green in combination with negative tests with TCNQ and gold chloride/NaOH indicates that a sample might contain MPA or one or more alkyloxy methylphosphonic acids, but not EMPTA or dithiane. Negative tests with Bromcresol Green and TCNQ combined with a positive gold chloride/NaOH test indicate that the sample may contain dithiane, but none of the phosphorus acids. Detection specificity is further improved when two or more tests are used in combination because different tests for the same analyte have different interference profiles.

TABLE 3

Results of Micro Spot Tests for Some Priority 1 Analytes

| | Reagent(s) for Micro Spot Test | | |
| --- | --- | --- | --- |
| Analyte | Bromcresol Green | TCNQ | Gold Chloride/NaOH |
| MPA | + | − | − |
| EMPA | + | − | − |
| IMPA | + | − | − |
| PMPA | + | − | − |
| EMPTA | + | + | + |
| DITHIANE | − | − | + |

Without additional data from other tests, however, the three spot tests used to obtain the data for Table 3, will not indicate if the unknown is a single substance or a mixture, and they will not indicate which phosphorus-containing acids may be present in the sample. However other tests could be used to provide more definitive results.

References

Detector Reagents

1. Jungreis, E., Spot Test Analysis: Clinical, Environmental, Forensic, and Geochemical Applications, Chemical Analysis, Volume 141, Second Edition, John Wiley and Sons, Inc., NY, 1997.
2. Mohammad, A., and Tiwari, S., Thirty-Five Years of Thin-Layer Chromatography in the Analysis of Inorganic Anions, Separation Science and Technology, 30(19), 3577–3614 (1995).
3. Jork, Helmut, Editor, Thin-Layer Chromatography: Reagents and Detection Methods, Vol. 1b, Physical and Chemical Detection Methods, John Wiley & Sons, NY, 1994.
4. Green F. J., The Sigma Aldrich Handbook of Stains, Dyes, and Indicators, Aldrich Chemical Co., 1990.
5. Novak, T. J., and Davis, P. M., Detection of Sulfur Mustards Using Spectrofluorometry, U.S. Pat. No. 5,032,380, 16 Jul. 1991.
6. Jork, Helmut, Editor, Thin-Layer Chromatography: Reagents and Detection Methods, Vol. 1a, Physical and Chemical Detection Methods, John Wiley & Sons, NY, 1989.
7. Novak, T. J., 4,4'-Dithiodianil, U.S. Pat. No. 4,414,414, Nov. 8, 1983.
8. Sherma, J., Practice and Applications of Thin Layer Chromatography on Whatman $KC_{18}$ Reversed Phase Plates, TLC Technical Series, Volume 1 (1981), Whatman Inc., Clifton, N.J. 07014.
9. Sass, S., and Ludemann, W., J. of Chromatography, 187, 447–452 (1980).
10. Gasparic, J., and Churacek, J., Detection Reagents, Laboratory Handbook of Paper and Thin Layer Chromatography, pp 323–335, Ellis Horwood, Ltd, England, 1978.
11. Corporate Authors, E. Merck, Dyeing Reagents for Thin Layer and Paper Chromatography, E. Merck, Darmstadt, Federal Republic of Germany, 1975.
12. Corporate Authors, Eastman Kodak Company, Eastman TLC Visualization Reagents and Chromatographic Solvents, Kodak Publication No. JJ-5 (1973), Eastman Kodak Company, Rochester, N.Y. 14650.
13. Zweig, G., and Sherma, J., Editors, Detection Reagents for Paper and Thin-Layer Chromatography, CRC Handbook of Chromatography, Volume II, Section II.I, pp 103–189, CRC Press, 1972.
14. Sawicki, E., Engel, C. R., and Elbert, W. C., Talanta 14, 1169–1178 (1967).
15. Ruch, W. E., Editor, Chemical Detection of Gaseous Pollutants: An Annotated Bibliography, Ann Arbor Science Publishers, Inc., Ann Arbor, Mich., 1966.
16. Feigl, F., Spot Tests in Organic Analysis, 6th Edition, Elsevier Science, Ltd., 1966.
17. Bryant, F., Overell, B. T., Biochim et Biophys. Acta 10, 471–6 (1963).
18. Feigl, F., Spot Tests in Inorganic Analysis, 7th Edition, Elsevier Science, Ltd, 1958.
19. Epstein, J., Rosenthal, R. W., and Ess, R. J., Anal. Chem. 27, 1435–39 (1955).
20. Bregoff, H. M., Roberts, E., Delwiche, C. C., J. Biol. Chem. 205, 565 (1953).
21. Munier, R. Bull. Soc. Chim. Biol. 35, 1225 (1953).
22. Obermiller, M., Angew. Chem. 49, 162–164 (1936).
23. Witten, B., and Prostak, A., Sensitive Detector Crayons for Phosgene, Hydrogen Cyanide, and Lewisite, Anal. Chem. 29, 885–7 (1957).
24. Pheil, R. W., Crayon for the Detection of G-Agents, U.S. Pat. No. 2,929, 791, Mar. 22, 1960.
25. Sass, S., Ludemann, W. D., Witten, B., Fischer, V., Sisti, A. J., and Miller, J. I., Colorimetric Determination of Certain Organophosphorus Compounds and Acylating Agents—Use of Diisonitrosoacetone Reagent, Anal. Chem. 29, 1346–9 (1957).
26. Kramer, D. N., and Morin, R. D., Detection of G-Agents, U.S. Pat. No. 2,926,072, Feb. 23, 1960.
27. Gehauf, B., Epstein, J., Wilson, G. B., Witten, B., Sass, S., Bauer, V. E., Rueggeberg, W. H. C., Anal. Chem. 29, 276 (1957).
28. Gehauf, B., and Goldenson, J., Detection and Estimation of Nerve Gases by Fluorescence Reaction, Anal. Chem. 29, 276 (1957).
29. Brante, G., Iodine as a Means of Development in Paper Chromatography, Nature 163, 651–2 (1949).
30. Sokolowski M., and Rozylo, J. K., TLC Analysis of Warfare Agents under Battlefield Conditions, Journal of Planar Chromatography 6, 467–71 (1993).
31. Munavalli, S., and Pannella, M., Thin-Layer Chromatography of Mustard and Its Metabolites, Journal of Chromatog., 437, 423–8 (1988).
32. Ellman, G. H., Arch. Biochem. Biophys., 82, 70–77 (1959).
33. Mikrochim Acta, 788 (1971); Ibid., 341 (1973).
34. Mikrochim Acta, 526 (1972).
35. Chemical and Engineering News, pg 29, Aug. 1, 1994.
36. Yoe, J. H., and Sarver, L. A., Organic Analytical Reagents, John Wiley, NY, 1941, pages 66–326.
37. Maile, R. J., Fishesser, G. J., and Anderson, M. M., Thin-Layer Chromatography of Phosphonic Acid Derivatives, Journal of Chromatog. 132, 366–68 (1977).
38. Reiner, M., ed. , Standard Methods of Clinical Chemistry, Vol. 1, Academic Press, NY, 1953, page 84.
39. T. E. Edmonds, J. M. Lee, and J. D. Lee, Dry Reagent Chemical Tests, Analytical Communications, 34, 1H–3H (1997).
40. A Zipp, W. E. Hornby, Solid Phase Chemistry: Its Principles And Applications In Clinical Analysis, Talanta 31, 863(1984).
41. E. Diebold, M. Rapkin, and A Usmani, Chemistry On A Stick (Part 1), Chemtech 21, 462 (1991).
42. A. Burke, J. DuBois, A. Azhar, and A. Usmani, Chemistry On A Stick (Part 2), Chemtech 21, 547 (1991).

What is claimed is:

1. A method of detecting the presence of an analyte, comprising the steps of:

placing a chromogenic or fluorogenic detector reagent for detecting the presence of the analyte on a chromatographic sheet or medium containing sorbent material selected from the group consisting of silica gel, high performance thin layer chromatography (HPTLC) silica gel, polysilicic acid, aluminum oxide, and mixtures of thereof;

placing the analyte in a solution where the solvent for the analyte consists of a non-aqueous solvent selected from the group of hexadecane, nonane, cyclohexane, trimethylpentane, petroleum ether, iso-hexanes, hexane, heptane, cyclopentane, trichlorotrifluoroethane, and pentane;

placing the solution containing the analyte in a tube having an end portion with a microcapillary sized opening, so that when the tube is placed in contact with a chromatographic sheet having a surface layer formed of sorbent material, the solution containing the analyte is withdrawn from the end portion of the tube and onto the surface layer of the sorbent material by capillary action;

placing the end portion of the tube having the microcapillary sized opening in contact with the sorbent material at the place where the detector reagent has been deposited on the sorbent material so that the solution containing the analyte is withdrawn from the tube by capillary action, the solvent being absorbed into the sorbent material and the analyte being separated from the solvent, and wherein the analyte remains at the spot of application and wherein the analyte is analyzed at this spot of application.

2. A method of screening a solution for an analyte that has been dissolved in a solvent to form the solution and for detecting the presence of the analyte when the solution is deposited in a sorbent material so that the analyte is separated from the solvent at the place of application to the sorbent material, comprising the steps of:

placing a detector reagent for detecting the presence of the analyte on the sorbent material;

placing the solution containing the analyte in a tube having an end portion forming a microcapillary sized opening in the end portion of the tube so that when the tube is placed in contact with the sorbent material, the solution containing the analyte in the tube is withdrawn from the end portion of the tube and into the sorbent material by capillary action;

placing the end portion of the tube forming the microcapillary sized opening in contact with the sorbent material at the location where the detector reagent is placed on the sorbent material, so that the solution is withdrawn from the tube by capillary action, the solvent being absorbed into the sorbent material and the analyte being separated from the solvent and adsorbed by the sorbent material at the spot of application, wherein the analyte remains at the spot of application and is analyzed at this same spot.

3. The method of claim 2, wherein the diameter of the microcapillary sized opening has range of diameters of from about 0.05 to about 1.6 millimeters.

4. The method of claim 2, wherein the sorbent material is formed of a polar material selected from the group consisting of silica gel, high performance thin layer chromatography (HPTLC) silica gel, polysilicic acid, and aluminum oxide and the solvent for the analyte is a non-aqueous solvent that is less polar than the sorbent material and selected from the group of ethylene dichloride, dichloromethane, ethyl ether, o-dichlorobenzene, chlorobenzene, benzene, o-xylene, m-xylene, p-xylene, methyl tertiary-butyl ether, toluene, carbon tetrachloride, trichloroethylene, n-butyl chloride, hexadecane, nonane, cyclohexane, trimethylpentane, petroleum ether, iso-hexanes, hexane, heptane, cyclopentane, trichlorotrifluoroethane, and pentane.

5. The method of claim 2, wherein the sorbent material comprises a thin layer chromatographic medium containing a silica gel or polysilicic acid sorbent and the solvent for the analyte is selected from the group consisting of hexadecane, nonane, cyclohexane, trimethylpentane, petroleum ether, iso-hexane, hexane, heptane, cyclopentane, trichlorotrifluoroethane, and pentane.

6. The method of claim 2, wherein the detector reagent is selected from the group of bromcresol green; 7,7,8,8-tetracyanoquinodimethane (TCNQ); gold chloride; gold chloride/NaOH solution; 4-(4'-nitrobenzyl)pyridine/NaOH; cholinesterase/indoxyl acetate; cholinesterase/2,6-dichloroindophenylacetate, sodium pyrophosphate peroxide/aromatic amine; potassium bismuth iodide; 1,3-diisonitrosoacetone guanidinium salt; bis(diethylamino) benzophenone oxime; bis(diethylamino)benzophenone; bis(dimethylamino)thiobenzophenone; phenylazoformic acid 2-diphenylhydrazide; diphenylcarbazone; diphenylthiocarbazone; mercuric salt; diethyldithiocarbamic acid silver salt; 2,2'-dithiobis(5-nitropyridine); 5,5'-dithiobis(2-nitrobenzoic acid), Ellman's Reagent; molybdenum oxide in sulfuric acid; ammonium molybdate; iodine/starch; and sulfuric acid (4M); ammonium sulfate; ammonium cerium(IV)sulfate; ammonium iron(II)sulfate; cobalt(II)thiocyanate; palladium (II)chloride; potassium iodide plateate; sodium tetraphenyl boron; o-tolidine; and N,2,6-trichloro-p-benzoquinoneimine.

7. The method of claim 6, wherein the sorbent material is a polar material selected from the group of silica gel, high performance thin layer chromatography (HPTLC) silica gel, polysilicic acid, and aluminum oxide, and the solvent for the analyte is selected from solvents that are less polar than the sorbent material and selected from the group consisting of ethylene dichloride, dichloromethane, ethyl ether, o-dichlorobenzene, chlorobenzene, benzene, o-xylene, m-xylene, p-xylene, methyl tertiary-butyl ether, toluene, carbon tetrachloride, trichloroethylene, n-butyl chloride, hexadecane, nonane, cyclohexane, trimethylpentane, petroleum ether, iso-hexanes, hexane, heptane, cyclopentane, trichlorotrifluoroethane, and pentane.

8. The method of claim 2, wherein the sorbent material is a chromatographic material selected from the group consisting of silica gel, high performance thin layer chromatography (HPTLC) silica gel, polysilicic acid, and aluminum oxide and mixtures thereof, and the solvent for the analyte is selected from the group consisting of hexadecane, nonane, cyclohexane, trimethylpentane, petroleum ether, iso-hexanes, hexane, heptane, cyclopentane, trichlorotrifluoroethane, and pentane.

9. The method of claim 2, wherein sorbent material is formed of a polar chromatographic material and the solvent for the analyte is a non-aqueous solvent that has a lower polarity than the sorbent material.

10. The method of claim 2, wherein the sorbent material is formed of a non-polar material selected from the group of reversed phase silica Gel $C_2$ (dimethyl bonded), reversed phase silica gel $C_2$ (ethyl bonded), reversed phase silica gel $C_8$ (octyl bonded), reversed phase silica gel $C_{18}$ (octadecyl bonded), acetylated cellulose, and the solvent for the analyte is an aqueous solvent mixture containing solvents selected from the from the group of water, methanol, acetonitrile, and acetone.

11. The method of claim 2, wherein the sorbent material is formed of an ion-exchange material selected from the group of anion exchange resin, cation exchange resin and diethylaminoethylcellulose and the solvent for the analyte comprises water.

12. A system for screening solutions containing an analyte and for detecting the presence of the analyte, comprising:

means for obtaining a solution containing the analyte;

tube means for receiving the solution containing the analyte, the tube means having an end portion with a microcapillary sized opening formed therein for dispensing the solution containing the analyte by capillary action;

sorbent material means having a detector reagent pre-deposited in the sorbent material for detecting the presence of the analyte, the sorbent material means receiving the solution containing the analyte from the tube means as the end portion of the tube means having the microcapillary sized opening is brought in contact with the sorbent material means so the solution containing the analyte is deposited on the sorbent material means by capillary action where the detector reagent has been pre-deposited and with the analyte being adsorbed by and concentrated in the sorbent material and remaining at the spot of contact between the end portion of the tube means with the sorbent material means for combining with the detector reagent.

13. The system according to claim 12, wherein the microcapillary sized opening is defined by an end wall of the end portion of the tube means and the thickness of the end wall is at least equal to the diameter of the microcapillary sized opening.

14. The system according to claim 12, wherein the microcapillary sized opening is defined by an end wall of the end portion of the tube means and the thickness of the end wall is at least twice the diameter of the microcapillary sized opening to reinforce the end portion of the tube means and to provide uniform sealing contact between the end wall and the sorbent material means when the tube means is placed in contact with the sorbent material means.

15. The system according to claim 12, wherein the tube means is selected from the group of microcapillary tubes, micropipets and micropipet tips.

16. The system according to claim 12, wherein the diameter of the microcapillary sized opening has range of between about 0.05 to about 1.6 millimeters.

17. The system according to claim 12, wherein the volume of a microcapillary tube or a micropipet is between about 0.1 to about 30 microliters.

18. The system according to claim 12, wherein the sorbent material means comprises a thin layer chromatographic sheet provided with a silica gel surface layer.

19. The system according to claim 12, wherein the sorbent material means comprises a thin layer chromatographic medium provided with a polysilicic acid sorbent.

20. The system according to claim 19, wherein the detector reagent is selected from the group consisting of bromcresol green; 7,7,8,8-tetracyanoquinodimethane (TCNQ); gold chloride; gold chloride/NaOH solution; 4-(4'-nitrobenzyl)pyridine/NaOH; cholinesterase/indoxyl acetate; cholinesterase/2,6-dichloroindophenyl acetate: sodium pyrophosphate peroxide/aromatic amine; potassium bismuth iodide; 1,3-diisonitrosoacetone guanidinium salt; bis(diethylamino)benzophenone oxime; bis(diethylamino)benzophenone; bis(dimethylamino)thiobenzophenone; phenylazoformic acid 2-diphenylhydrazide; diphenylcarbazone; diphenylthiocarbazone; mercuric salt; diethyldithiocarbamic acid silver salt; 2,2'-dithiobis(5-nitropyridine); 5,5'-dithiobis(2-nitrobenzoic acid), Ellman's Reagent; molybdenum oxide in sulfuric acid; ammonium molybdate; iodine/starch; and sulfuric acid (4M), ammonium sulfate; ammonium cerium(IV)sulfate; ammonium iron(II)sulfate; cobalt(II) thiocyanate; palladium(II)chloride; potassium iodine plateate; sodium tetraphenyl boron; o-tolidine; and N,2,6-trichloro-p-benzoquinoneimine.

21. The system according to claim 12, wherein the sorbent material is formed of a polar silica gel material and the solvent for the solution containing the analyte is a non-aqueous solvent that has a lower polarity than the sorbent material.

22. The system according to claim 12, wherein the sorbent material is a polar material selected from the group consisting of silica gel, high performance thin layer chromatography (HPTLC) silica gel, polysilicic acid, and aluminum oxide and the solvent for the analyte is a non-aqueous solvent that is selected from the group comprising hexadecane, nonane, cyclohexane, trimethylpentane, petroleum ether, iso-hexanes, hexane, heptane, cyclopentane, trichlorotrifluoroethane, and pentane.

23. The system according to claim 12, wherein the detector reagent comprises a solution in which the detector reagent is dissolved in a polar solvent and deposited on the sorbent material, wherein the sorbent material is a polar material selected from the group of silica gel, high performance thin layer chromatography (HPTLC) silica gel, polysilicic acid, and aluminum oxide and wherein the solvent for the analyte is less polar than the sorbent material and is selected from the group comprising hexadecane, nonane, cyclohexane, trimethylpentane, petroleum ether, iso-hexanes, hexane, heptane, cyclopentane, trichlorotrifluoroethane, and pentane.

24. The system according to claim 12, wherein the sorbent material is a chromatographic material selected from the group consisting of silica gel, high performance thin layer chromatography (HPTLC) silica gel, polysilicic acid, aluminum oxide, cellulose, polyamide, reversed phase silica Gel $C_2$ (dimethyl bonded), reversed phase silica gel $C_2$ (ethyl bonded), reversed phase silica gel $C_8$ (octyl bonded), reversed phase silica gel $C_{18}$ (octadecyl bonded), acetylated cellulose, silica gel modified with amino groups, silica gel modified with cyano groups, Kieselghur impregnated with hydrocarbons, anionic and cationic anion exchange resins, diethylaminoethyl cellulose, and mixtures of the listed sorbents, and the solvent for the analyte is selected from the group comprising acetic acid, water, aqueous buffer solution with a pH in the range 2–12, dimethylsulfoxide, N-methylpyrrolidone, N,N-dimethyl acetamide, N,N-dimethyl formamide, propylene carbonate, acetonitrile, 2-methoxyethanol, diethylcarbonate, pyridine, methanol, acetone, ethanol, beta-phenethylamine, 2-ethoxyethanol, dioxane, methyl ethyl ketone, methyl n-propyl ketone, methyl acetate, methyl isobutyl ketone, chloroform, tetrahydrofuran, n-propanol, methyl isoamyl ketone, ethyl acetate, 2-methoxyethylacetate, isobutyl alcohol, n-butyl acetate, 2-butanol, 2-propanol, 1-butanol, ethylene dichloride, dichloromethane, ethyl ether, o-dichlorobenzene, chlorobenzene, benzene, o-xylene, m-xylene, p-xylene, methyl tertiary-butyl ether, toluene, carbon tetrachloride, trichloroethylene, n-butyl chloride, hexadecane, nonane, cyclohexane, trimethylpentane, petroleum ether, iso-hexanes, hexane, heptane, cyclopentane, trichlorotrifluoroethane, and pentane.

25. The method of claim 2, wherein the sorbent material comprises a porous medium formed of two layers, the top layer formed of a sorbent substance and a detector reagent on or within a porous support, and wherein the analyte is deposited in the top layer, and the bottom layer is formed a porous absorbent material containing a compound that dissolves in water to form a solution that wets the top layer, and the compound in aqueous solution reacts with the substance produced due to the reaction or interaction of the analyte with the detector reagent in the top layer, thereby producing a color change, or a change in fluorescence under ultraviolet illumination.

26. The system according to claim 12, wherein the sorbent material comprises a porous medium formed of two layers, the top layer formed of a sorbent substance and a detector reagent on or within a porous support, and wherein the analyte is deposited in the top layer, and the bottom layer is formed a porous absorbent material containing a compound that dissolves in water to form a solution that wets the top layer, and the compound in aqueous solution reacts with the substance produced due to the reaction or interaction of the analyte with the detector reagent in the top layer, thereby producing a color change, or a change in flourescence under ultraviolet illumination.

* * * * *